(12) United States Patent
Sugawara et al.

(10) Patent No.: US 8,847,138 B2
(45) Date of Patent: Sep. 30, 2014

(54) IMAGING APPARATUS, IMAGING SYSTEM, AND METHOD FOR CONTROLLING IMAGING APPARATUS

(71) Applicant: Canon Kabushiki Kaisha, Tokyo (JP)

(72) Inventors: Eriko Sugawara, Honjo (JP); Toshio Kameshima, Kumagaya (JP); Tomoyuki Yagi, Honjo (JP); Katsuro Takenaka, Honjo (JP); Sho Sato, Kumagaya (JP); Atsushi Iwashita, Honjo (JP); Hideyuki Okada, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 119 days.

(21) Appl. No.: 13/623,566

(22) Filed: Sep. 20, 2012

(65) Prior Publication Data

US 2013/0082166 A1 Apr. 4, 2013

(30) Foreign Application Priority Data

Sep. 29, 2011 (JP) ............... PCT/JP2011/072322

(51) Int. Cl.
| | |
|---|---|
| H04N 5/359 | (2011.01) |
| A61B 6/00 | (2006.01) |
| H04N 5/32 | (2006.01) |
| H04N 5/321 | (2006.01) |
| G01T 1/24 | (2006.01) |
| H04N 5/374 | (2011.01) |

(52) U.S. Cl.
CPC .... *A61B 6/00* (2013.01); *H04N 5/359* (2013.01); *H04N 5/3205* (2013.01); *H04N 5/32* (2013.01); *A61B 6/4233* (2013.01); *H04N 5/321* (2013.01); *G01T 1/247* (2013.01); *A61B 6/487* (2013.01); *H04N 5/374* (2013.01)
USPC ............... 250/208.1; 250/370.08; 250/370.09

(58) Field of Classification Search
USPC .......................... 250/208.1, 370.08, 370.09
See application file for complete search history.

(56) References Cited

FOREIGN PATENT DOCUMENTS

| | | | |
|---|---|---|---|
| JP | 10253761 | A | 9/1998 |
| JP | 2002199278 | A | 7/2002 |
| JP | 2003194949 | A | 7/2003 |
| JP | 2005303586 | A | 10/2005 |
| JP | 2005354640 | A | 12/2005 |

*Primary Examiner* — Tony Ko
(74) *Attorney, Agent, or Firm* — Canon USA, Inc. IP Division

(57) ABSTRACT

An imaging apparatus includes a detector having a plurality of conversion elements for converting radiation or light into an electric charge, a power supply unit that supplies a first voltage to the conversion element in a first imaging operation, and a control unit that controls the detector and the power supply unit. During a period between the first imaging operation and a second imaging operation, the control unit controls to perform a first inter-imaging operation in which a second voltage different from the first voltage is supplied to the conversion element, and, subsequently to the first inter-imaging operation, a second inter-imaging operation in which a third voltage different from the first and the second voltages is supplied to the conversion element. The absolute value of the difference between the third and the first voltages is smaller than the absolute value of the difference between the second and the first voltages.

13 Claims, 13 Drawing Sheets

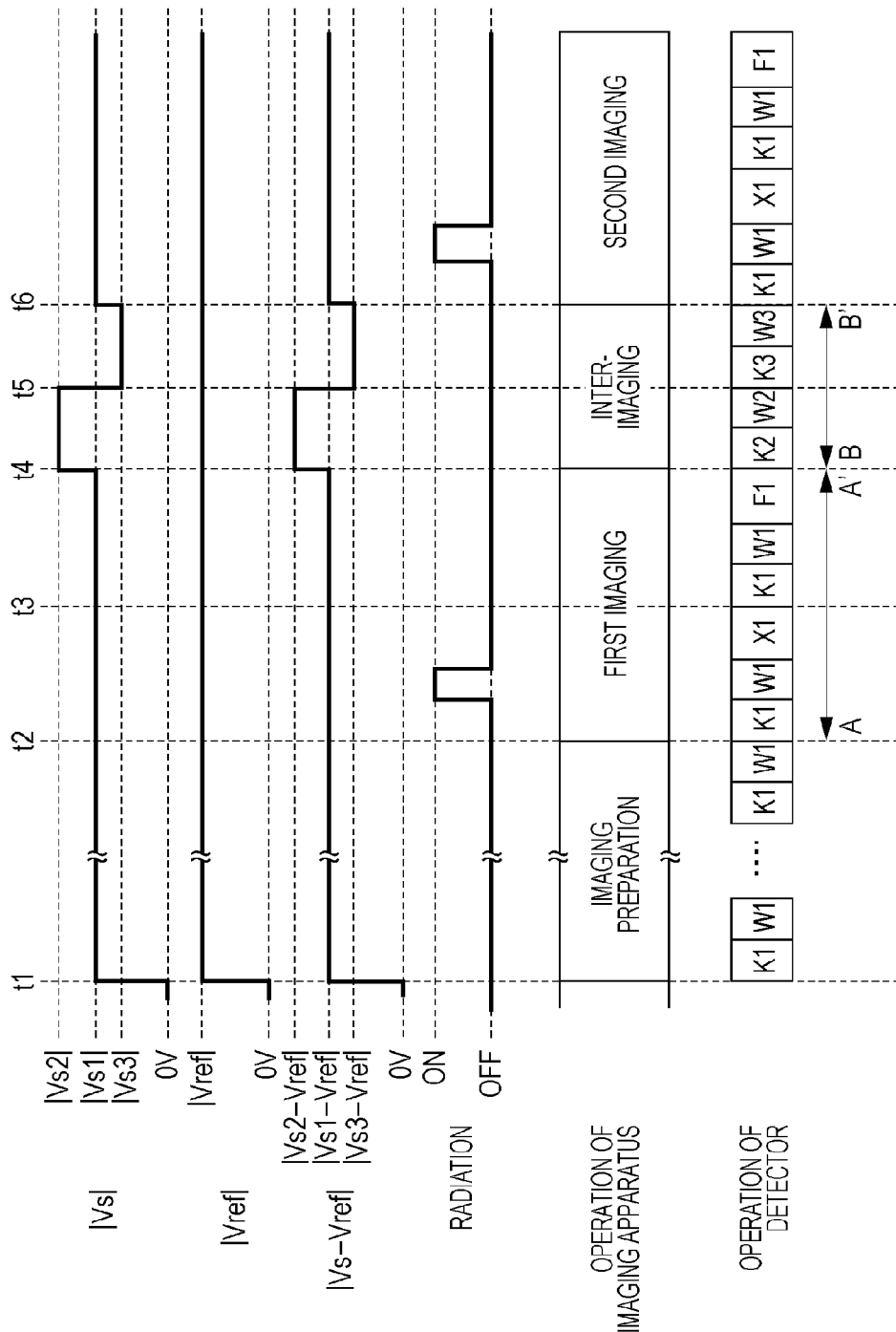

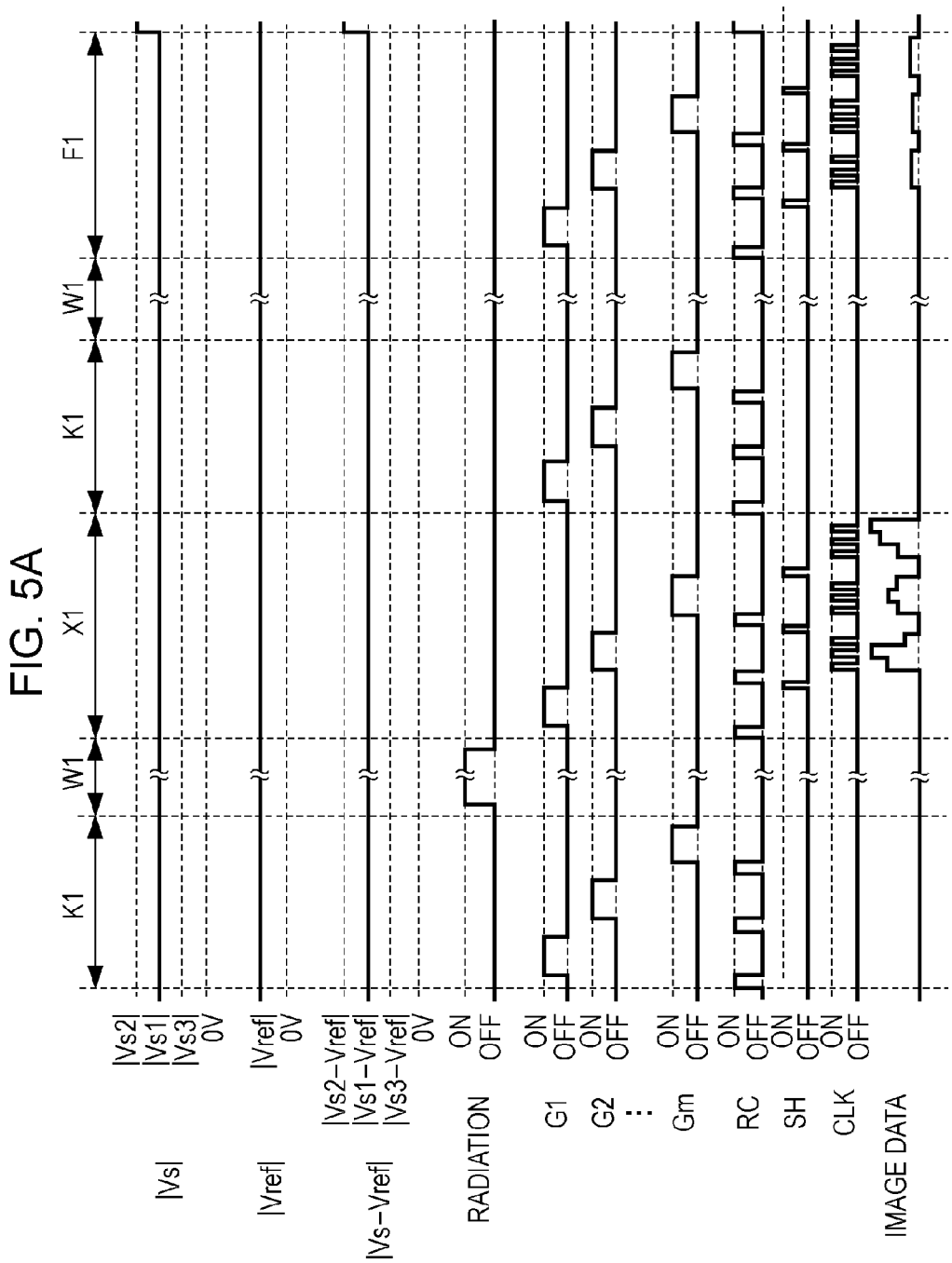

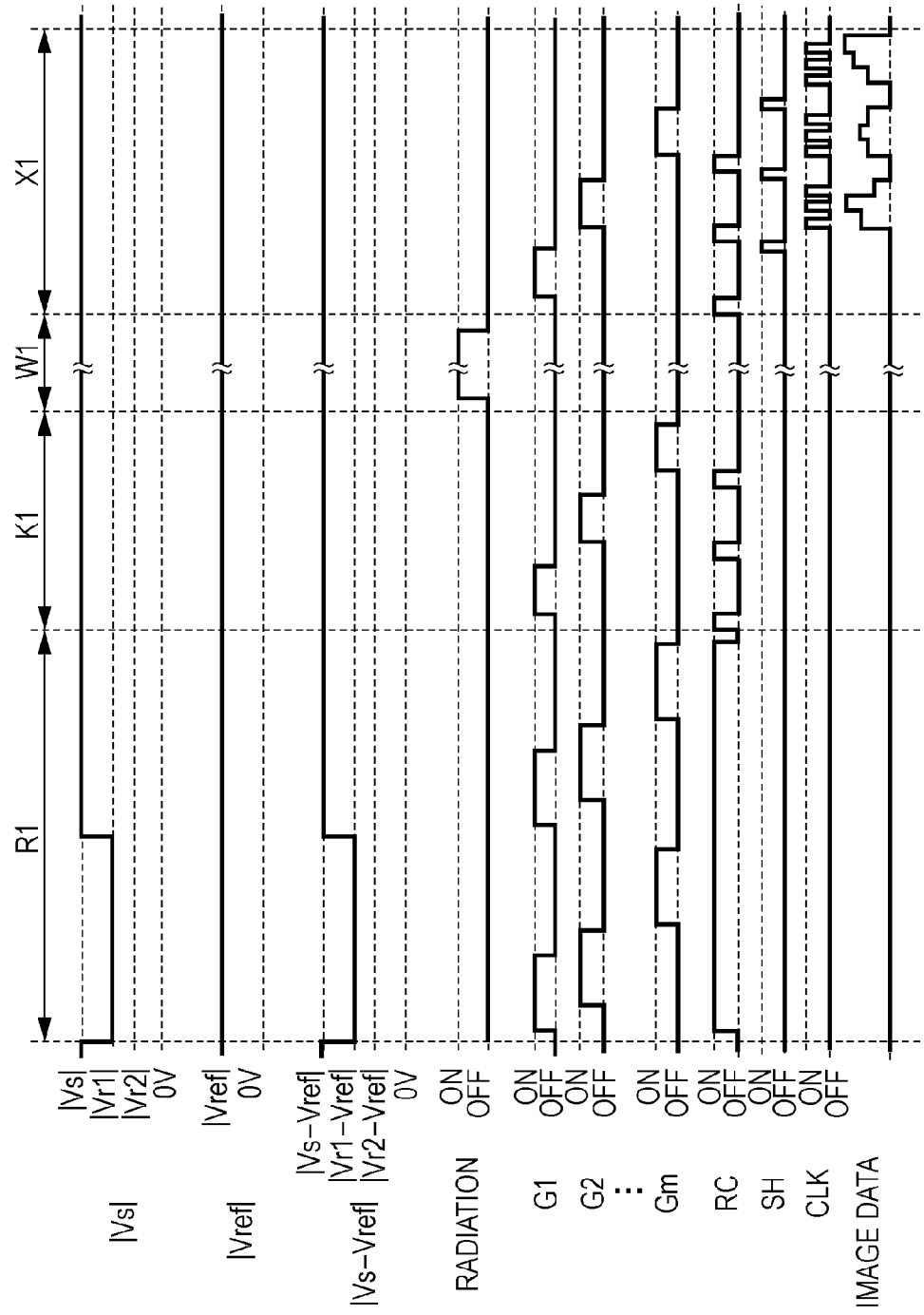

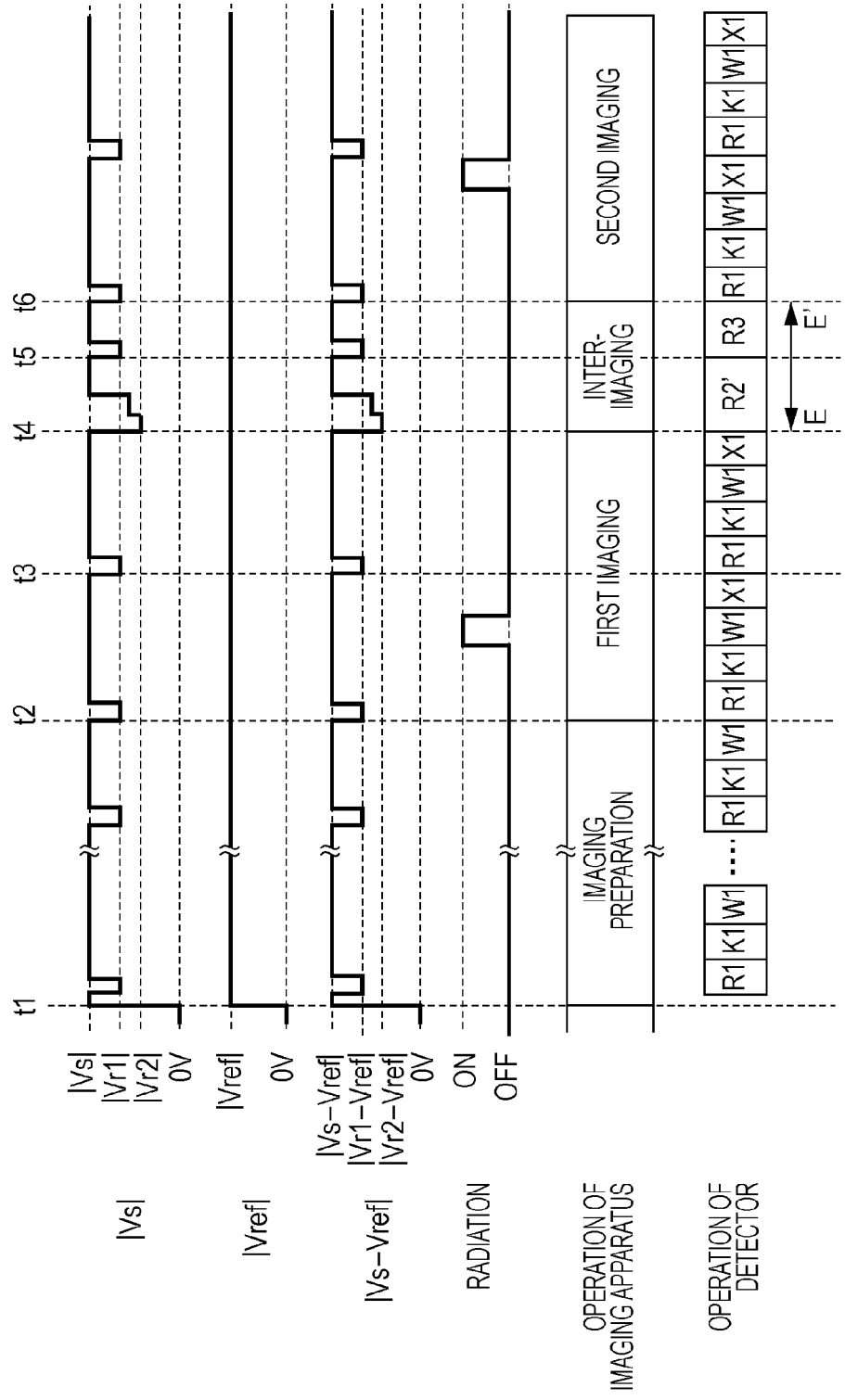

IMAGING APPARATUS, IMAGING SYSTEM, AND METHOD FOR CONTROLLING IMAGING APPARATUS

TECHNICAL FIELD

The present invention relates to an imaging apparatus and an imaging system, and a method for controlling the same. More specifically, the present invention relates to a radiation imaging apparatus and a radiation imaging system, and a method for controlling the same, which are suitable for use in still image radiography such as general imaging in medical diagnosis or moving image radiography such as fluoroscopic imaging.

BACKGROUND ART

In recent years, radiation imaging apparatuses using a flat panel detector (FPD) formed of semiconductor materials have been put into practical use as imaging apparatuses to be used for X-ray based medical imaging diagnosis or non-destructive testing. Hereinafter, flat panel detectors will be generally referred to as "detectors". In, for example, medical imaging diagnosis, such radiation imaging apparatuses have been used as digital imaging apparatuses for still image radiography such as general imaging or moving image radiography such as fluoroscopic imaging. Known detectors include an indirect conversion detector using a conversion element including, in combination, a photoelectric conversion element made of amorphous silicon and a wavelength conversion member that converts radiation into light of a wavelength band detectable by the photoelectric conversion element. Other known detectors include a direct conversion detector using a conversion element that is made of a material such as amorphous selenium and that converts radiation directly into charge.

In such imaging apparatuses, for a conversion element having a semiconductor layer made of amorphous semiconductor, a dangling bond or defect in the semiconductor layer acts as a trap level. When imaging is performed a plurality of times, charge generated by radiation or light applied in the preceding imaging operation may be trapped in the trap level. In this case, a so-called afterimage (lag), which is affected by the charge trapped in an image obtained in the subsequent imaging operation, may occur in the image obtained in the subsequent imaging operation. The afterimage may be prevented by extending the time between the preceding imaging operation and the subsequent imaging operation (hereinafter referred to as the imaging operation interval); however, if the imaging operation interval is increased, usability is impaired. For this reason, an imaging apparatus is demanded which prevents an afterimage from occurring in the subsequent imaging while reducing the imaging operation interval.

Patent Literature (PTL) documents 1 and 2 disclose a reset operation of supplying a voltage different from that in the imaging operation to a conversion element such as a photodiode or an MIS photoelectric conversion element during a plurality of imaging operations in order to prevent an afterimage. Specifically, in PTL 1, a reverse voltage larger or smaller than a reverse voltage to a photodiode during an imaging operation, or a forward voltage during a reset operation is supplied to the photodiode during a reset operation. In PTL 2, a voltage different from that during an imaging operation is supplied to an MIS photoelectric conversion element so that both electrodes of the MIS photoelectric conversion element are grounded during a sleep (reset) operation. It is disclosed in PTLs 1 and 2 that charge which may cause an afterimage is removed from the conversion element by using the reset operation.

CITATION LIST

Patent Literature

PTL 1: Japanese Patent Laid-Open No. 10-253761
PTL 2: Japanese Patent Laid-Open No. 2002-199278

In the conventional reset operation described above, it is possible to prevent an afterimage; however, the current flowing into the conversion element during the reset operation may increase noise, resulting in reduced S/N ratio. It is suggested in PTL 2 that the duration of the reset operation or the voltage during the reset operation are optimized so as to achieve the effect of preventing an afterimage and to reduce the current flowing into the conversion element after the reset operation. However, the optimization of the duration of the reset operation and the voltage during the reset operation may make it difficult to achieve both the prevention of afterimage and the maintenance of sufficient S/N ratio.

The exemplary embodiments of the present invention are intended to solve the above problems involved in the conventional structure, and aims to provide an imaging apparatus capable of acquiring an image with a high S/N ratio while preventing an afterimage even with short imaging operation intervals.

SUMMARY OF INVENTION

An imaging apparatus according to embodiments of the present invention is an imaging apparatus including a detector including a plurality of conversion elements each having a first electrode, a second electrode, and a semiconductor layer disposed between the first electrode and the second electrode and converting radiation or light into charge, the detector performing an imaging operation of outputting an electrical signal based on the charge; a power supply unit that supplies a first voltage to the conversion elements for enabling the conversion elements to convert the radiation or light into the electric charge in the imaging operation to the conversion elements; and a control unit that controls the detector and the power supply unit, wherein the control unit controls the detector and the power supply unit to perform a first inter-imaging operation in which a second voltage different from the first voltage is supplied to the conversion elements, during a period between, in the imaging operation which is performed a plurality of times, a first imaging operation and a second imaging operation subsequent to the first imaging operation, and a second inter-imaging operation in which a third voltage different from the first voltage and the second voltage is supplied, during the period, subsequently to the first inter-imaging operation, and wherein the absolute value of the difference between the third voltage and the first voltage is smaller than the absolute value of the difference between the second voltage and the first voltage.

An imaging system according to the present invention includes the above-described imaging apparatus, and a control computer that sends a control signal to the above-described control unit.

A method for controlling an imaging apparatus according to the present invention is a method for controlling an imaging apparatus including a detector including a plurality of conversion elements each having a first electrode, a second electrode, and a semiconductor layer disposed between the first electrode and the second electrode and converting radiation or light into charge, the method including the steps of performing a first imaging operation for allowing the detector to output an electrical signal based on the charge converted from the radiation or light by the conversion element to which a first voltage for allowing the conversion element to convert radiation or light into charge has been supplied; performing subsequently to the first imaging operation a first inter-imaging operation in which a second voltage different from the first voltage is supplied to the conversion element; performing subsequently to the first inter-imaging operation a second inter-imaging operation in which a third voltage different from the first voltage and the second voltage is supplied to the conversion element; and performing subsequently to the second inter-imaging operation a second imaging operation for allowing the detector to output an electrical signal based on the charge converted from radiation or light by the conversion element to which the first voltage has been supplied, wherein the absolute value of the difference between the third voltage and the first voltage is smaller than the absolute value of the difference between the second voltage and the first voltage.

Further features of the present invention will become apparent from the following description of exemplary embodiments with reference to the attached drawings.

BRIEF DESCRIPTION OF DRAWINGS

FIG. 1 is a timing chart of an imaging apparatus according to a first embodiment of the present invention.

FIG. 5A is a timing chart of the imaging apparatus according to the first embodiment of the present invention.

FIG. 9A is a timing chart of the imaging apparatus according to the second embodiment of the present invention.

FIG. 10A is a timing chart of another example of the imaging apparatus according to the second embodiment of the present invention.

DESCRIPTION OF EMBODIMENTS

Embodiments of the present invention will be described in detail hereinafter with reference to the drawings. In the present invention, it is assumed that radiation includes, in addition to $\alpha$ rays, $\beta$ rays, and $\gamma$ rays, which are beams of particles (including photons) emitted by radiative decay, beams having energy higher than or equal to that of the above rays, for example, X-rays, particle beams, cosmic rays, and others.

First Embodiment

Figure 2A:
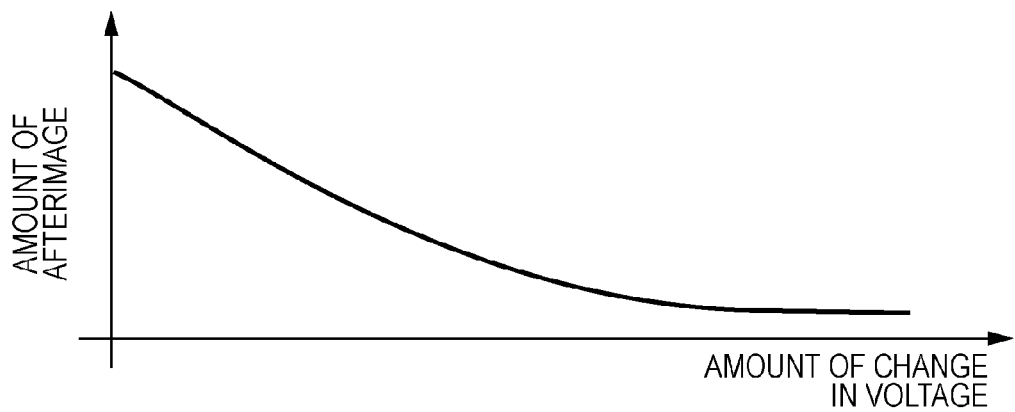
FIG. 2A is a characteristic diagram depicting the dependence of the amount of afterimage on changes in voltage of a conversion element according to the first embodiment of the present invention.
Figure 2B:
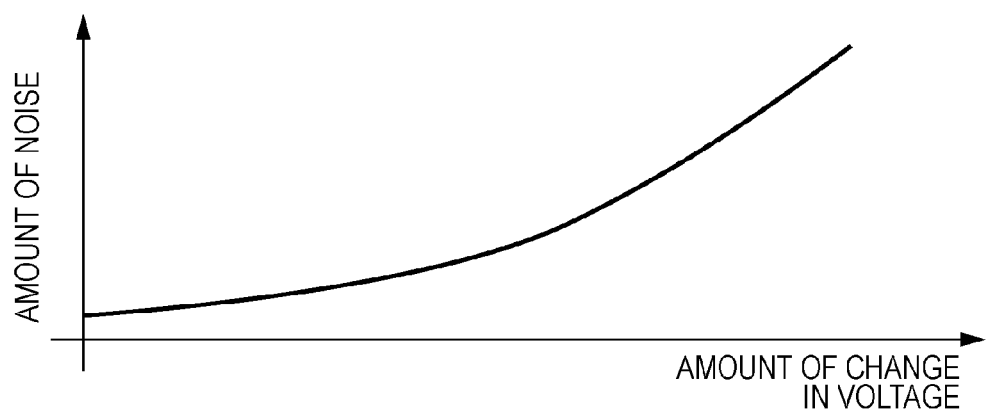
FIG. 2B is a characteristic diagram depicting the dependence of the amount of noise on changes in voltage of the conversion element according to the first embodiment of the present invention.

First, in order to explain the concept of the present invention, the characteristics on the amount of afterimage of a conversion element according to a first embodiment of the present invention and a characteristic of the amount of noise will be described with FIGS. 2A and 2B, respectively.

The conversion element has a semiconductor layer between two facing electrodes, and is capable of converting radiation or light into charge by supplying a voltage between the two electrodes. Here, the voltage to be supplied between the two electrodes of the conversion element is a voltage to be supplied to the conversion element. In an imaging operation including a period during which radiation or light is applied, a voltage (hereinafter referred to as the first voltage) for depleting the semiconductor layer is supplied between the two electrodes as the voltage to be supplied to the conversion element. Thus, the conversion element is able to convert radiation or light into charge.

Indices for determining the quality of an electrical signal to be output from a detection unit including a plurality of conversion elements, and image data to be output from a detector including the detection unit may include an amount of noise and an amount of afterimage. Noise is a random fluctuation component contained in a signal separately from original information, and the main causes of noise in the conversion element may include dark current. The dark current may be caused by causing a current to flow in the conversion element when the voltage to be supplied to the conversion element varies and causing the movement of the charge due to the current to influence the defect level. In addition, afterimage is a phenomenon in which an electrical signal based on irradiation with radiation or light in the preceding imaging operation among a plurality of imaging operations has an effect on an electrical signal and image data output in the subsequent imaging operation. The main causes of afterimage may include charge trapped in the defect level, and charge not output from the conversion element and left on the conversion element.

As described in the background section, it is possible to prevent an afterimage by supplying a voltage (hereinafter referred to as the second voltage) different from the first voltage to the conversion element during a plurality of imaging operations. As illustrated in FIG. 2A, as the difference (hereinafter referred to as the amount of change in voltage) between the first voltage and the second voltage to be supplied to the conversion element during a plurality of imaging operations increases, the amount of afterimage, which is the quantity of afterimage, is reduced. Here, in FIG. 2A, the horizontal axis represents the absolute value of the amount of change in voltage, and the vertical axis represents the amount of afterimage. The reason for this can be considered to be that charge is injected into the conversion element by the current flowing into the conversion element in accordance with the change in the voltage to be supplied to the conversion element, and thus charge can be trapped in the defect level in advance so as to prevent additional charge that is converted by radiation or light from being trapped. The reason can also be considered to be that residual charge in the conversion element is removed through recombination or the like with charge to be injected into the conversion element by the current flowing into the conversion element. That is, as the amount of change in voltage increases, the quantity of charge (the amount of charge) to be injected into the conversion element increases, and the amount of afterimage decreases. In contrast, as illustrated in FIG. 2B, as the amount of change in voltage increases, the amount of noise, which is the quantity of noise, increases. Here, in FIG. 2B, the horizontal axis represents the absolute value of the amount of change in voltage, and the vertical axis represents the amount of noise. The reason for this can be considered to be that as the current flowing into the conversion element increases in accordance with the change in the voltage to be supplied to the conversion element, the amount of dark current generated accordingly increases. That is, the larger the amount of change in voltage, the larger the amount of charge to be injected into the conversion element, resulting in the increased amount of noise.

Accordingly, as the amount of change in voltage increases to reduce the amount of afterimage, the amount of charge to be injected into the conversion element increases and the amount of noise increases, resulting in the reduced S/N ratio of the imaging apparatus. In this case, if the subsequent imaging is performed until the noise has settled down in order to reduce the amount of noise, the period of time until the subsequent imaging is performed is increased, resulting in the reduced usability of the imaging apparatus. In contrast, as the amount of change in voltage decreases, the amount of charge to be injected into the conversion element is decreased and the amount of afterimage is increased, resulting in insufficient prevention of afterimage.

Figure 3:
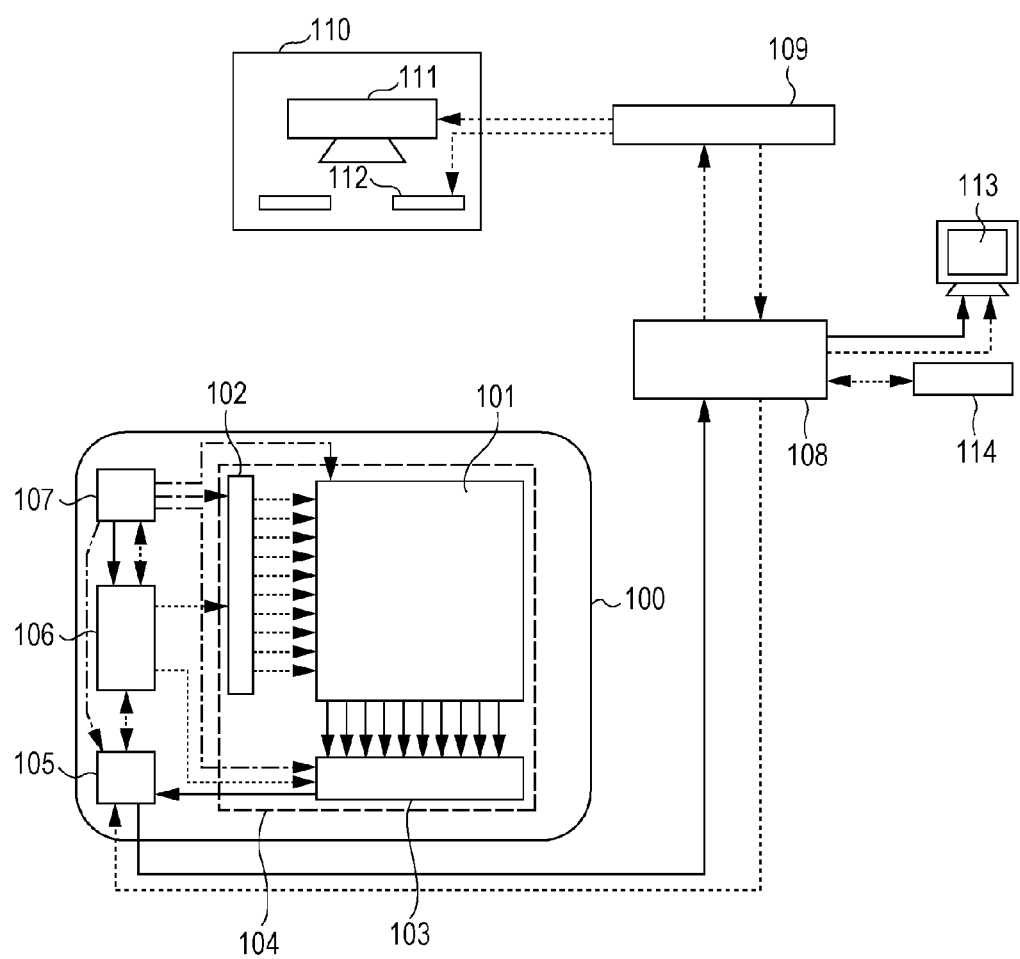
FIG. 3 is a schematic block diagram of an imaging system according to the present invention.

As a result of intensive study, the present inventor has found the following. A detector is controlled so that, as illustrated in FIG. 1, in a plurality of imaging operations including a first imaging operation and a second imaging operation subsequent to the first imaging operation, the detector performs an inter-imaging operation between the first imaging operation and the second imaging operation. In the inter-imaging operation, the detector is controlled so that the detector first performs a first inter-imaging operation during the period between the first imaging operation and the second imaging operation. In the first inter-imaging operation, the detector is controlled so that a second voltage different from a first voltage to be supplied to the conversion element in each imaging operation is supplied to the conversion element and the detector performs at least an initialization operation for initializing the conversion element. Here, the term initialization operation refers to an operation for supplying a desired voltage to the conversion element, and an operation for, in a configuration of a pixel including a conversion element and a switching element as illustrated in FIG. 3, bringing the switching element into a conductive state separately from an image output operation and a dark image output operation described below. The absolute value of the difference between the second voltage and the first voltage is defined as an amount of change in the first voltage. Here, the amount of change in the first voltage is set larger than an amount of change in the second voltage described below. In this way, in the first inter-imaging operation, a large amount of change in voltage is supplied to the conversion element, thereby allowing afterimage to be reduced as desired. In the first inter-imaging operation, however, since a large change in voltage is supplied to the conversion element, the amount of charge to be injected into the conversion element is increased, resulting in the increased noise. Then, the detector is controlled so that the detector performs a second inter-imaging operation during the period between the first inter-imaging operation and the second imaging operation. In the second inter-imaging operation, the detector is controlled so that a third voltage different from the first voltage and the second voltage is supplied to the conversion element and the detector performs an initialization operation. The absolute value of the difference between the third voltage and the first voltage is defined as an amount of change in the second voltage. Here, the amount of change in the second voltage is set smaller than the amount of change in the first voltage. The second inter-imaging operation can reduce the amount of charge to be injected into the conversion element, and can reduce noise increased in the first inter-imaging operation. Therefore, the present inventor has found that by performing the first inter-imaging operation and the second inter-imaging operation subsequent to the first inter-imaging operation between the first imaging operation and the second imaging operation, it is possible to prevent an increase in noise while reducing the afterimage generated in the preceding imaging operation. Each operation will be described in detail below.

Next, a radiation imaging system according to the first embodiment will be described with reference to FIG. 3. The radiation imaging system according to the present invention illustrated in FIG. 3 includes an imaging apparatus 100, a control computer 108, a radiation control device 109, a radiation generation device 110, a display device 113, and a console 114. The imaging apparatus 100 includes a flat panel detector 104 including a detection unit 101 having a plurality of pixels each converting radiation or light into an electrical signal, a drive circuit 102 that drives the detection unit 101, and a read circuit 103 that outputs the electrical signal from the driven detection unit 101 as image data. The imaging apparatus 100 further includes a signal processing unit 105 that processes image data from the flat panel detector (detector) 104 and outputs a result, a control unit 106 that supplies a control signal to each component and controls the operation of the detector 104, and a power supply unit 107 that supplies a bias to each component. The signal processing unit 105 receives a control signal from the control computer 108, described below, and provides the control signal to the control unit 106. In response to the control signal received from the control computer 108, the control unit 106 controls at least one of the drive circuit 102, the read circuit 103, the signal processing unit 105, and the power supply unit 107. The power supply unit 107 contains a power supply circuit such as a regulator that receives a voltage from an external power supply or an internal battery (not illustrated) and that supplies a voltage necessary for the detection unit 101, the drive circuit 102, and the read circuit 103. The power supply unit 107 according to this embodiment is a variable power supply capable of switching among at least the first voltage, the second voltage, and the third voltage and supplying either voltage to the conversion element of the detection unit 101.

The control computer 108 performs synchronization between the radiation generation device 110 and the imaging apparatus 100, sends a control signal to determine the state of the imaging apparatus 100, and performs image processing to correct, save, and display the image data from the imaging apparatus 100. The control computer 108 further sends a control signal to the radiation control device 109 to determine the radiation irradiation conditions on the basis of the information from the console 114.

In response to a control signal from the control computer 108, the radiation control device 109 controls the operation of applying radiation from a radiation source 111 contained in the radiation generation device 110 and the operation of a radiation field aperture mechanism 112. The radiation field aperture mechanism 112 has a function capable of changing a predetermined radiation field that is a region irradiated with radiation or light corresponding to radiation in the detection unit 101 of the detector 104. The console 114 receives input of information concerning a subject or imaging conditions as parameters for various control operations of the control computer 108, and transmits the input parameters to the control computer 108. The display device 113 displays image data subjected to image processing by the control computer 108.

Figure 4:
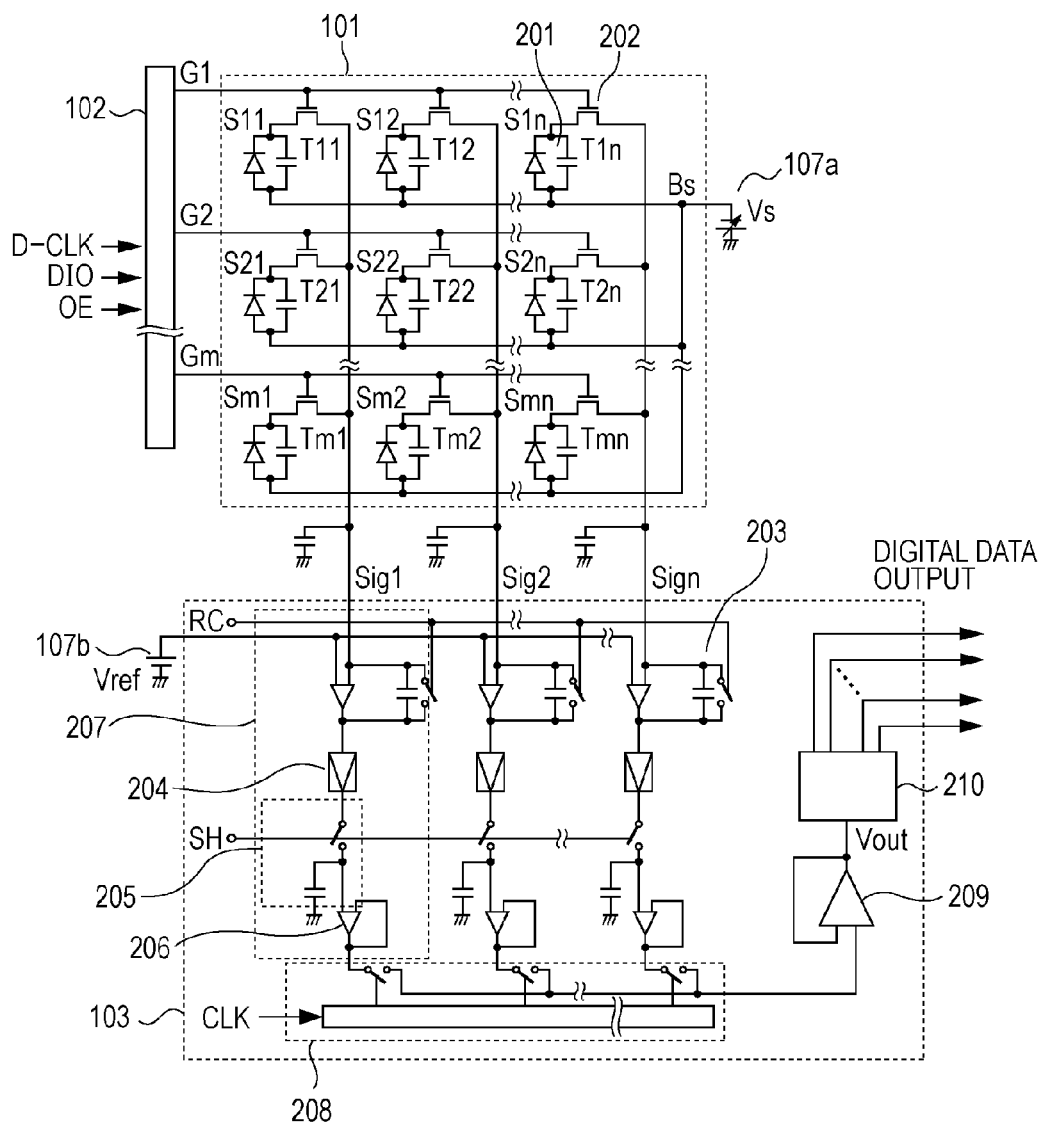
FIG. 4 is a schematic equivalent circuit diagram of the imaging apparatus according to the first embodiment of the present invention.

Next, an imaging apparatus according to the first embodiment of the present invention will be described with reference to FIG. 4. The same configurations as those described with reference to FIG. 3 are assigned the same numerals and the detailed description thereof is omitted.

The detection unit 101 has a plurality of pixels arranged in a two-dimensional matrix of m rows and n columns, but a one-dimensional matrix may also be applicable. Each pixel has a conversion element 201 that converts radiation or light into an electric charge, and a switching element 202 that outputs an electrical signal corresponding to the electric charge. Suitable examples of the conversion element may include an indirect conversion element including a photoelectric conversion element that converts light into charge and a wavelength conversion member disposed on the radiation-incident side thereof that converts radiation into light of a wavelength band detectable by the photoelectric conversion element, and a direct conversion element that converts radiation directly into charge. In this embodiment, a PIN photodiode disposed on an insulating substrate such as a glass substrate and including amorphous silicon as a main component is used as a photodiode that is one type of photoelectric conversion element. Suitable examples of the switching element 202 may include a transistor including a control terminal and two main terminals, and, in this embodiment, a thin film transistor (TFT) is used. One electrode (first electrode) of the conversion element 201 is electrically connected to one of the two main terminals of the switching element 202, and the other electrode (second electrode) is electrically connected to a first power supply 107a via a common bias line Bs. A plurality of switching elements in the row direction, for example, T11 to T1n, have control terminals electrically connected to commonly a drive line G1 in the first row, and are supplied with drive signals for controlling the conductive state of the switching elements on a row-by-row basis from the drive circuit 102 via drive lines. The other main terminals of a plurality of switching elements in the column direction, for example, T11 to Tm1, are electrically connected to a signal line Sig1 in the first column, and electrical signals corresponding to the charge of the conversion elements are output to the read circuit 103 via signal lines while the switching elements are in the conductive state. A plurality of signal lines Sig1 to Sign arranged in the column direction transmit the electrical signals output from the plurality of pixels to the read circuit 103 in parallel.

The read circuit 103 is provided with amplifier circuits 207 for the individual signal lines to amplify the electrical signals output in parallel from the detection unit 101. Each of the amplifier circuits 207 includes an integrating amplifier 203 that amplifies the output electrical signal, a variable amplifier 204 that amplifies the electrical signal from the integrating amplifier 203, a sample and hold circuit 205 that samples and holds the amplified electrical signal, and a buffer amplifier 206. The integrating amplifier 203 includes an operational amplifier that amplifies and outputs the read electrical signal, an integrating capacitor, and a reset switch. The integrating amplifier 203 is capable of changing the amplification factor by changing the value of the integrating capacitor. The operational amplifier has an inverting input terminal to which the output electrical signal is input, a non-inverting input terminal to which a reference potential Vref is input from a second power supply 107b, and an output terminal from which the amplified electrical signal is output. Further, the integrating capacitor is disposed between the inverting input terminal and the output terminal of the operational amplifier. The sample and hold circuit 205 is provided for each amplifier circuit, and includes a sampling switch and a sampling capacitor. The read circuit 103 further includes a multiplexer 208 that sequentially outputs the electrical signals read in parallel from the amplifier circuits 207 and that outputs the electrical signals as a serial image signal, and a buffer amplifier 209 that impedance-converts and outputs the image signal. An image signal Vout that is an analog electrical signal output from the buffer amplifier 209 is converted into digital image data by an A/D converter 210, and is output to the signal processing unit 105. The image data processed by the signal processing unit 105 is output to the control computer 108.

The drive circuit 102 outputs a drive signal having a conductive voltage Vcom for bringing the switching elements into a conductive state and a non-conductive voltage Vss for bringing the switching elements into a non-conductive state to each drive line in accordance with control signals (D-CLK, OE, DIO) input from the control unit 106. Thus, the drive circuit 102 controls the conductive state and non-conductive state of the switching elements, and drives the detection unit 101.

The power supply unit 107 includes the first power supply 107a and the second power supply 107b for the amplifier circuits. The first power supply 107a is configured to commonly supply a potential Vs to the second electrodes of the individual conversion elements via the bias line Bs, and corresponds to a first power supply according to the present invention. The second power supply 107b is configured to supply a reference potential Vref to the non-inverting input terminals of the individual operational amplifiers, and corresponds to a second power supply according to the present invention. The reference potential Vref is supplied to the first electrodes of the conversion elements 201 via the signal lines Sig1 to Sign and the switching elements 202 when the switching elements are in the conductive state. In this embodiment, the first power supply 107a is a variable power supply capable of switching among at least a first potential Vs1, a second potential Vs2, and a third potential Vs3 and supplying either potential to the pixels of the detection unit 101. However, the present invention is not limited to this, and the second power supply 107b may be a variable power supply capable of switching among at least a first reference potential Vref1, a second reference potential Vref2, and a third reference potential Vref3 and supplying either potential to the pixels.

In response to a control signal from the control computer 108 or the like outside the apparatus via the signal processing unit 105, the control unit 106 supplies various control signals to the drive circuit 102, the power supply unit 107, and the read circuit 103, and controls the operation of the detector 104. The control unit 106 supplies a control signal D-CLK, a control signal OE, and a control signal DIO to the drive circuit 102 to control the operation of the drive circuit 102. Here, the control signal D-CLK is a shift clock for a shift register to be used as a drive circuit, the control signal DIO is a pulse transferred by the shift register, and the control signal OE is configured to control the output terminal of the shift register. The control unit 106 further supplies a control signal RC, a control signal SH, and a control signal CLK to the read circuit 103 to control the operation of the individual components of the read circuit 103. Here, the control signal RC is configured to control the operation of the reset switches of the integrating amplifiers, the control signal SH is configured to control the operation of the sample and hold circuit 205, and the control signal CLK is configured to control the operation of the multiplexer 208.

Figure 5B:
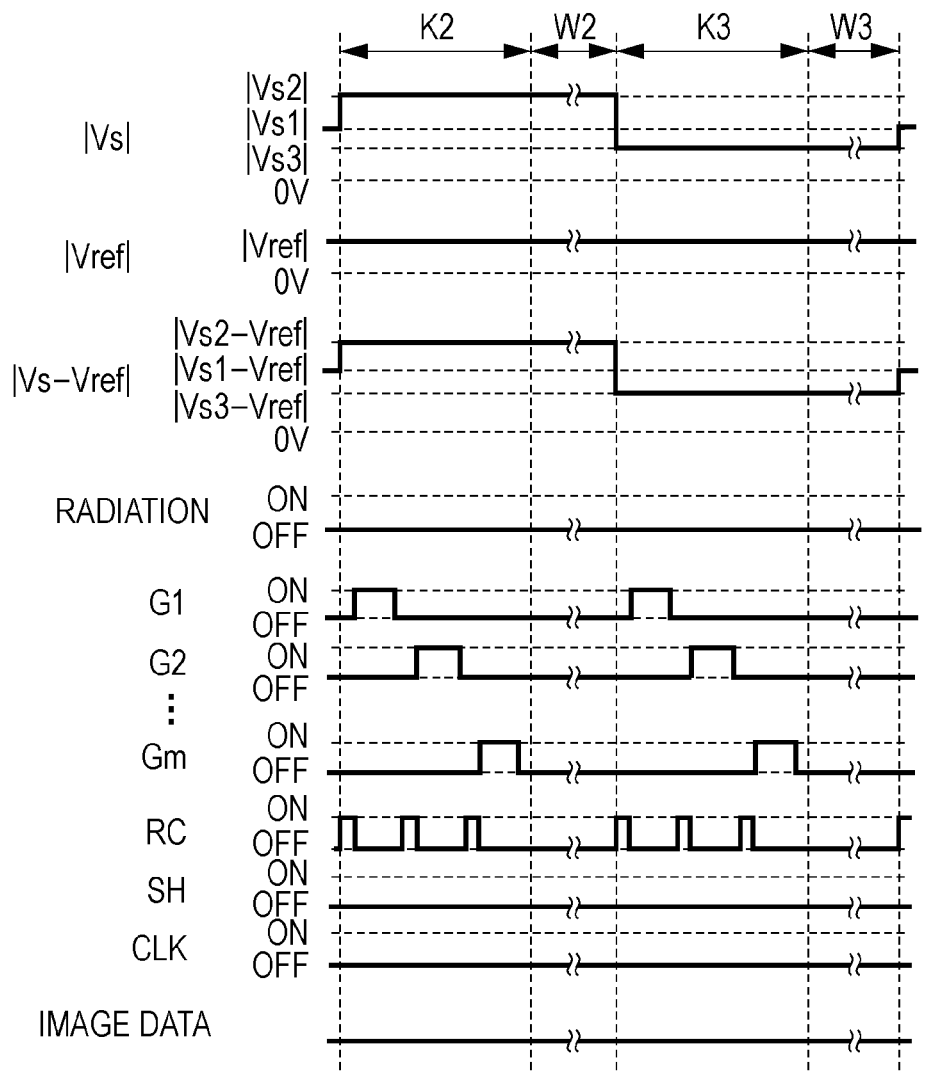
FIG. 5B is a timing chart of the imaging apparatus according to the first embodiment of the present invention.

Next, the operation of an imaging apparatus according to the present invention will be described with reference to FIGS. 1, 5A, and 5B. Here, FIG. 5A illustrates the A-A' section in FIG. 1 in detail, and FIG. 5B illustrates the B-B' section in FIG. 1 in detail.

As illustrated in FIG. 1, when the first potential Vs1 is supplied to the conversion elements 201 at time t1, the imaging apparatus 100 performs an imaging preparation operation during an imaging preparation period. Here, the imaging preparation operation is an operation of performing an initialization operation K at least once in order to stabilize noise in the detector 104, which is caused by starting the application of the first potential Vs1, and, in this embodiment, the initialization operation K1 is repeatedly performed a plurality of times. If the change in the characteristics of the detector 104 is stable, the imaging preparation operation may not be performed. Here, the term initialization operation refers to an operation of bringing a plurality of switching elements in a detection unit into a conductive state sequentially row by row or in units of a plurality of rows at a time, separately from an image output operation and a dark image output operation described below, in order to supply a desired voltage to initialize the conversion elements in the detection unit. In this embodiment, the initialization operation K1 is performed by supplying an initial voltage prior to an accumulation operation, that is, a first voltage |Vs1–Vref|, to the conversion elements. In FIG. 1, an operation of repeatedly performing a set of the initialization operation K1 and an accumulation operation W1 a plurality of times is performed as the imaging preparation operation. In the present invention, the accumulation operation is an operation in which charge is accumulated in the conversion elements, and, in this embodiment, is performed by bringing all the switching elements of the plurality of pixels into a non-conductive state. In this embodiment, it is assumed that Vs1=–8 (V), Vref=3 (V), and the conversion elements 201 have been supplied with a reverse voltage.

Then, at time t2 after a predetermined time period has elapsed since time t1, the imaging apparatus 100 starts the first imaging operation. During the period from time t2 to time t3 within an imaging period from time t2 to time t4, the imaging apparatus 100 performs the initialization operation K1, the accumulation operation W1, and an image output operation X1. In the imaging operation, the accumulation operation W1 is an operation performed during a period in accordance with the application of radiation in order to allow the conversion elements to generate charge, and the image output operation X is an operation of outputting image data in accordance with an electrical signal corresponding to the charge generated in the accumulation operation W. While, in this embodiment, the accumulation operation in each imaging operation is performed for the same time length as that of the accumulation operation in the imaging preparation operation, the present invention is not limited to this. For a reduction in the time required for the imaging preparation operation, it is preferable that the time length of the accumulation operation in the imaging preparation operation be shorter than the time length of the accumulation operation in the imaging operations. In this embodiment, furthermore, the initialization operation in the imaging operations is performed with the same voltage for the same time length as those of the initialization operation in the imaging preparation operation. However, the present invention is not limited to this. For a reduction in the time required for the imaging preparation operation, it is preferable that the time length of the initialization operation in the imaging preparation operation be shorter than the time length of the initialization operation in the imaging operations. Then, during the period from time t3 to time t4, an accumulation operation W1 that is performed for the same time length as that of the accumulation operation W1 prior to the image output operation X1, and a dark image output operation F1 for outputting dark image data based on the charge generated in the preceding accumulation operation W1 are performed. These operations are performed in order to allow the conversion elements to generate charge in a dark state where no radiation is applied. In the dark image output operation F1, an operation similar to the image output operation X1 is performed in the imaging apparatus 100.

Then, when the first imaging operation is completed at time t4, the imaging apparatus 100 performs an inter-imaging operation until time t6 when the next imaging operation is started. The inter-imaging operation includes a first inter-imaging operation performed during the period from time t4 to time t5, and a second inter-imaging operation performed during the period from time t5 to time t6. In the first inter-imaging operation performed during the period from time t4 to time t5, a second voltage |Vs2–Vref| is supplied to the conversion elements 201, and at least the initialization operation K2 is performed. In this embodiment, the initialization operation K2 and the accumulation operation W2 are performed in the first inter-imaging operation. Here, an amount of change in the first voltage |Vs2–Vs1|, which is the difference between the second voltage and the first voltage, is larger than an amount of change in the second voltage |Vs3–Vs1|, described below, which is the difference between the third voltage and the first voltage. In the first inter-imaging operation, therefore, a large amount of change in voltage is supplied to the conversion elements, thereby reducing afterimage as desired. In the first inter-imaging operation, however, noise is increased because a large change in voltage is supplied to the conversion element. Thus, a second inter-imaging operation is performed during the period from time t5 to time t6. In the second inter-imaging operation, an amount of change in the second voltage |Vs3–Vs1| smaller than the amount of change in the first voltage |Vs2–Vs1| is supplied to the conversion elements 201, and at least an initialization operation K3 is performed. In this embodiment, the initialization operation K3 and an accumulation operation W3 are performed in the second inter-imaging operation. Here, the initialization operations K2 and K3 are similar to the initialization operation K1 described above, except that the voltage to be supplied to the conversion element is different from that in the initialization operation K1. In addition, the accumulation operations W2 and W3 are also similar to the accumulation operation W1 described above, except that the voltage to be supplied to the conversion elements is different from that in the accumulation operation W1. In the second inter-imaging operation, therefore, an amount of change in voltage smaller than that in the first inter-imaging operation is supplied to the conversion elements, thereby reducing noise, which has been increased in the first inter-imaging operation. In this manner, the first inter-imaging operation and the second inter-imaging operation subsequent to the first inter-imaging operation are performed during the period between the first imaging operation and the second imaging operation, thereby making it possible to prevent an increase in noise while reducing afterimage that has occurred in the first imaging operation. In this embodiment, it is assumed that |Vs2−Vs1|=5 (V) and |Vs3−Vs1|=2 (V), where Vs2=−13 (V) and Vs3=−6 (V).

Next, the respective imaging operations will be described in detail with reference to FIG. 5A. The operations descried above are not described. As illustrated in FIG. 5A, in the initialization operation K1, first, the control signal RC is supplied from the control unit 106 to the reset switches, and the integrating capacitors and the signal lines of the integrating amplifier 203 are reset. Then, the conductive voltage Vcom is supplied from the drive circuit 102 to the drive line G1 while the first potential Vs1 is being supplied to the conversion elements 201, and the switching elements T11 to T13 of the pixels in the first row are brought into a conductive state. The conductive state of the switching elements allows the voltage |Vs1−Vref| to be supplied to the conversion elements, and the conversion elements are initialized. In this case, the charge of the conversion elements is output as electrical signals by the switching elements. However, in this embodiment, the control signal SH and the control signal CLK are not output, and the circuits downstream of the sample and hold circuits are not activated. Thus, the data corresponding to the electrical signals is not output from the read circuit 103. After that, the integrating capacitors and the signal lines are reset again, and therefore the output electrical signals are processed. If the data is used for correction or the like, the control signal SH and the control signal CLK may be output and the circuits downstream of the sample and hold circuits may be activated in a manner similar to that in the image output operation or the dark image output operation described below. Such control of the conductive state of the switching elements and reset as above is repeatedly performed until the m-th row, resulting in the initialization operation K1 of the detector 104 being performed. Here, in the initialization operation K1, the reset switches may be maintained in the conductive state even during at least the conductive state of the switching elements and may continue resetting. In addition, the conduction time of the switching elements in the initialization operation K1 may be shorter than the conduction time of the switching elements in the image output operation X1 described below. Furthermore, switching elements in a plurality of rows may be simultaneously brought into conduction in the initialization operation K1. In the above cases, the time required for the overall initialization operation K1 can be reduced, and the change in the characteristics of the detector can be stabilized more quickly. Next, in the accumulation operation W1, the non-conductive voltage Vss is supplied to the switching elements 202 while the voltage |Vs1−Vref| is being supplied to the conversion elements 201, and the switching elements of all the pixels are brought into a non-conductive state. In this state, the conversion elements are irradiated with radiation, thus allowing charge based on the radiation to be accumulated in the conversion elements. Next, in the image output operation X1, first, the control signal RC is output from the control unit 106, and the integrating capacitors and the signal lines are reset. Then, the conductive voltage Vcom is supplied from the drive circuit 102 to the drive line G1, and the switching elements T11 to T1n in the first row are brought into a conductive state. Thus, electrical signals based on the charge generated in the conversion elements S11 to S1n in the first row are output to the individual signal lines. The electrical signals output in parallel via the individual signal lines are amplified by the integrating amplifiers 203 and the variable amplifiers 204 of the respective amplifier circuits 207. The amplified electrical signals are held in parallel in the sample and hold circuits 205 in the respective amplifier circuits 207, where the sample and hold circuits have been activated by the control signal SH. After the electrical signals are held, the control signal RC is output from the control unit 106, and the integrating capacitors and the signal lines of the integrating amplifiers 203 are reset. After the integrating capacitors and the signal lines are reset, the conductive voltage Vcom is supplied to the drive line G2 in the second row in a manner similar to that in the first row, and the switching elements T21 to T2n in the second row are brought into a conductive state. During the period during which the switching elements T21 to T2n in the second row are brought into a conductive state, the multiplexer 208 sequentially outputs the electrical signals held in the sample and hold circuit 205. Thus, the electrical signals read in parallel from the pixels in the first row are converted into a serial image signal and are output, and the A/D converter 210 converts the serial image signal into image data for one row and outputs the image data. The above operation is performed on the first row to the m-th row on a row-by-row basis, and therefore image data of one frame is output from the imaging apparatus.

After that, as illustrated in FIG. 5A, the initialization operation K1 is performed again. Then, the accumulation operation W1 is performed in the state where the conversion elements are not irradiated with radiation, and charge not based on radiation is accumulated in the conversion elements. After that, in the dark image output operation F1, an operation similar to the image output operation X1 is performed in the imaging apparatus 100 in a dark state where no radiation is applied, dark image data not based on radiation is obtained.

Next, the respective inter-imaging operations will be described in detail with reference to FIG. 5B. As illustrated in FIG. 5B, in the initialization operation K2, first, the control signal RC is supplied from the control unit 106 to the reset switches, and the integrating capacitors and the signal lines of the integrating amplifiers 203 are reset. Then, the conductive voltage Vcom is supplied from the drive circuit 102 to the drive line G1 while the voltage Vs2 is being supplied to the conversion elements 201, and the switching elements T11 to T13 of the pixels in the first row are brought into a conductive state. The conductive state of the switching elements allows the voltage |Vs2−Vref| to be supplied to the conversion element, and the afterimage of the conversion element is reduced. In this case, the charge of the conversion elements is output as electrical signals by the switching elements. However, in this embodiment, the control signal SH and the control signal CLK are not output, and the circuits downstream of the sample and hold circuits are not activated. Thus, the data corresponding to the electrical signals is not output from the read circuit 103. After that, the integrating capacitors and the signal lines are reset again, and therefore the output electrical signals are processed. If the data is used for correction or the like, the control signal SH and the control signal CLK may be output and the circuits downstream of the sample and hold circuits may be activated in a manner similar to that in the image output operation X1 or the dark image output operation F1. Such control of the conductive state of the switching elements and reset as above is repeatedly performed until the m-th row, resulting in the initialization operation K2 of the detector 104 being performed. Here, in the initialization operation K2, the reset switches may be maintained in the conductive state even during at least the conductive state of the switching elements and may continue resetting. In addition, the conduction time of the switching elements in the initialization operation K2 may be shorter than the conduction time of the switching elements in the image output operation. Furthermore, switching elements in a plurality of rows may be simultaneously brought into conduction in the initialization operation K2. In the above cases, the time required for the overall initialization operation K2 can be reduced, and the afterimage in the detector can be stabilized more quickly. In this embodiment, the initialization operation K2 is performed at the same time intervals as those of the image output operation X1. In the accumulation operation W2, the non-conductive voltage Vss is supplied to the switching elements 202 while the voltage |Vs2−Vref| is being supplied to the conversion elements 201, and the switching elements of all the pixels are brought into a non-conductive state.

Next, as illustrated in FIG. 5B, in the initialization operation K3, first, the control signal RC is supplied from the control unit 106 to the reset switches, and the integrating capacitors and the signal lines of the integrating amplifiers 203 are reset. Then, the conductive voltage Vcom is supplied from the drive circuit 102 to the drive line G1 while the voltage Vs3 is being supplied to the conversion elements 201, and the switching elements T11 to T13 of the pixels in the first row are brought into a conductive state. The conductive state of the switching elements allows the voltage |Vs3−Vref| to be supplied to the conversion element, and the noise in the conversion element is reduced. In this case, the charge of the conversion elements is output as electrical signals by the switching elements. However, in this embodiment, the control signal SH and the control signal CLK are not output, and the circuits downstream of the sample and hold circuits are not activated. Thus, the data corresponding to the electrical signals is not output from the read circuit 103. After that, the integrating capacitors and the signal lines are reset again, and therefore the output electrical signals are processed. If the data is used for correction or the like, the control signal SH and the control signal CLK may be output and the circuits downstream of the sample and hold circuits may be activated in a manner similar to that in the image output operation X1 or the dark image output operation F1. Such control of the conductive state of the switching elements and reset as above is repeatedly performed until the m-th row, resulting in the initialization operation K3 of the detector 104 being performed. Here, in the initialization operation K3, the reset switches may be maintained in the conductive state even during at least the conductive state of the switching elements and may continue resetting. In addition, the conduction time of the switching elements in the initialization operation K3 may be shorter than the conduction time of the switching elements in the image output operation X1. Furthermore, switching elements in a plurality of rows may be simultaneously brought into conduction in the initialization operation K3. In the above cases, the time required for the overall initialization operation K3 can be reduced, and the noise in the detector can be stabilized more quickly. In this embodiment, the initialization operation K3 is performed at the same time intervals as those of the image output operation X1. In the accumulation operation W3, the non-conductive voltage Vss is supplied to the switching elements 202 while the voltage |Vs3−Vref| is being supplied to the conversion elements 201, and the switching elements of all the pixels are brought into a non-conductive state.

In this embodiment, it is assumed that Vs2=−13 (V) and Vs3=−6 (V) and that a reverse voltage is supplied to the conversion elements in any case. However, the present invention is not limited to this. For example, it may be assumed that |Vs2−Vs1|=5 (V) and |Vs3−Vs1|=2 (V), where Vs2=−3 (V) and Vs3=−6 (V). That is, a reverse voltage smaller than that during the imaging operation may be supplied during the first inter-imaging operation, and a reverse voltage smaller than that during the imaging operation and larger than that during the first inter-imaging operation may be supplied during the second inter-imaging operation. It may also be assumed that, for example, |Vs2−Vs1|=12 (V) and |Vs3−Vs1|=2 (V), where Vs2=4 (V) and Vs3=−6 (V). In this case, when Vs2=4 (V), a forward voltage is supplied to the conversion element. That is, a forward voltage may be supplied during the first inter-imaging operation, and a reverse voltage smaller than that during the imaging operation may be supplied during the second inter-imaging operation. It may also be assumed that, for example, |Vs2−Vs1|=5 (V) and |Vs3−Vs1|=1 (V), where Vs2=−13 (V) and Vs3=−9 (V). That is, a reverse voltage larger than that during the imaging operation may be supplied during the first inter-imaging operation, and a reverse voltage larger than that during the imaging operation and smaller than that during the first inter-imaging operation may be supplied during the second inter-imaging operation. It may also be assumed that, for example, |Vs2−Vs1|=5 (V) and |Vs3−Vs1|=1 (V), where Vs2=−3 (V) and Vs3=−9 (V). That is, a reverse voltage smaller than that during the imaging operation may be supplied during the first inter-imaging operation, and a reverse voltage larger than that during the imaging operation may be supplied during the second inter-imaging operation. In addition, in each inter-imaging operation, only an initialization operation may be performed without accumulation operations being performed. In this case, the voltage to be supplied to the conversion element may be gradually changed. That is, in the present invention, during the period between the first imaging operation and the second imaging operation, at least the first inter-imaging operation and the second inter-imaging operation may be performed during the period between the first imaging operation and the second inter-imaging operation and during the period between the first inter-imaging operation and the second imaging operation, respectively.

Second Embodiment

Figure 6A:
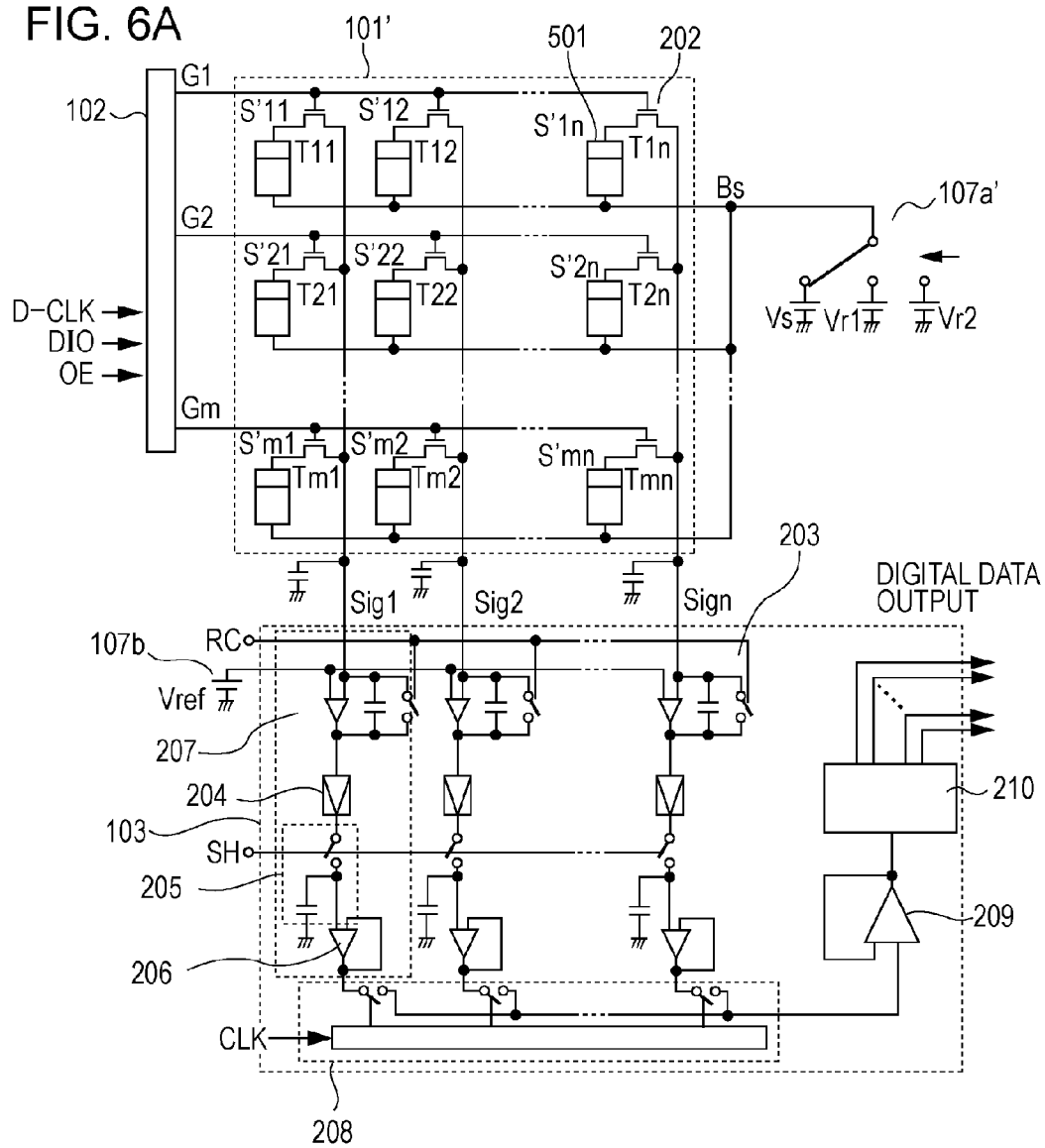
FIG. 6A is a schematic equivalent circuit diagram of an imaging apparatus according to a second embodiment of the present invention.
Figure 6B:
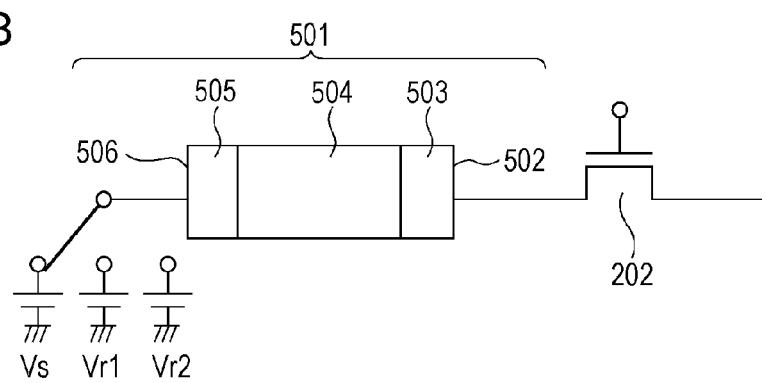
FIG. 6B is a schematic equivalent circuit diagram of the imaging apparatus according to the second embodiment of the present invention.

Next, an imaging apparatus according to a second embodiment of the present invention will be described with reference to FIGS. 6A and 6B. The same configurations as those according to the first embodiment described with reference to FIG. 3 are assigned the same numerals and the detailed description thereof is omitted. FIG. 6B illustrates a schematic equivalent circuit of one pixel.

While in the detection unit 101 according to the first embodiment, a PIN photodiode is used for each of the conversion elements 201, in a detection unit 101' according to this embodiment, an MIS photoelectric conversion element is used for each of conversion elements 501 as an MIS conversion element. In addition, in the first embodiment, the other electrodes of the conversion elements 201 are electrically connected to the first power supply 107a via the common bias line Bs. In this embodiment, in contrast, the other electrodes of conversion elements 501 are electrically connected to a first power supply 107a' via a common bias line Bs. The first power supply 107a' is configured to be capable of supplying a second potential Vr1 for refreshing conversion elements 501 and a third potential Vr2, separately from the first potential Vs for allowing the conversion elements to generate charge, to the other electrodes of the conversion elements 501 in a multivalued manner.

As illustrated in FIG. 6B, furthermore, each of the conversion elements 501 has a semiconductor layer 504 between a first electrode 502 and a second electrode 506, and an insulating layer 503 between the first electrode 502 and the semiconductor layer 504. Each of the conversion elements 501 further has an impurity semiconductor layer 505 between the semiconductor layer 504 and the second electrode 506. The second electrode 506 is electrically connected to the first power supply 107a' via the bias line Bs. In each of the conversion elements 501, as in each of the conversion elements 201, the first potential Vs is supplied to the second electrode 506 from the first power supply 107a', and the reference potential Vref is supplied to the first electrode 502 via the switching element 202. Thus, an accumulation operation is performed. Further, a refresh potential Vr (Vr1 or Vr2) is supplied to the second electrode 506 via the first power supply 107a', and the conversion element 501 is refreshed by the voltage |Vr−Vref|. Refresh means that electrons or holes in electron-hole pairs generated in the semiconductor layer 504 of the MIS conversion element and accumulated between the semiconductor layer 504 and the insulating layer 503 without passing through the impurity semiconductor layer 505 are caused to move towards the second electrode 506 and annihilate. The details of refreshing will be described below.

Figure 7A:
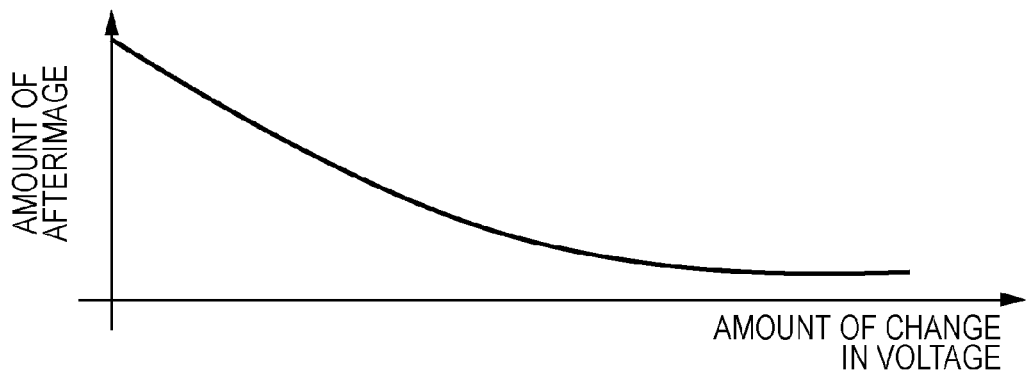
FIG. 7A is a characteristic diagram depicting the dependence of the amount of afterimage on changes in voltage of a conversion element according to the second embodiment of the present invention.
Figure 7B:
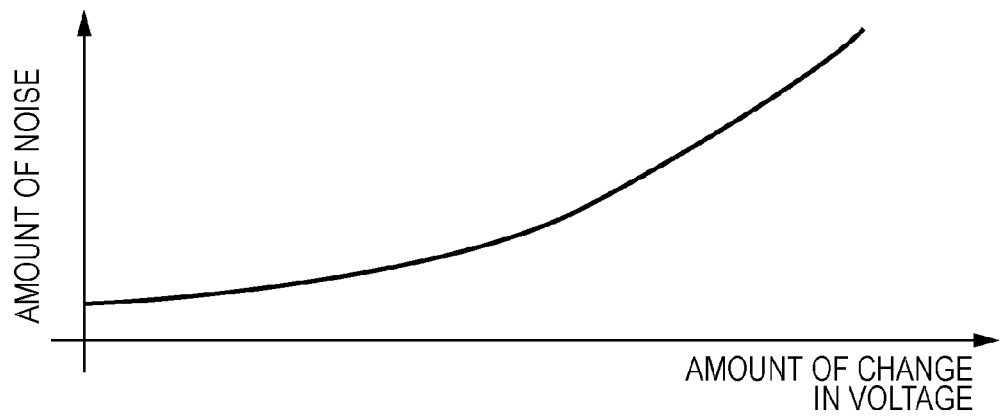
FIG. 7B is a characteristic diagram depicting the dependence of the amount of noise on changes in voltage of the conversion element according to the second embodiment of the present invention.

Next, the characteristics of the amount of afterimage and the characteristics on the amount of noise of a conversion element according to the second embodiment of the present invention will be described with reference to FIGS. 7A and 7B, respectively, in order to describe the concept of the present invention in this embodiment.

Also in the MIS conversion element, similarly to the one described in the first embodiment, a second voltage (|Vr−Vref|) different from a first voltage (|Vs−Vref|) is supplied to the conversion element in a plurality of imaging operations, thereby making it possible to prevent an afterimage. As illustrated in FIG. 7A, as the amount of change in voltage to be supplied to the conversion element in a plurality of imaging operations increases, the amount of afterimage is reduced. Here, in FIG. 7A, the horizontal axis represents the absolute value of the amount of change in voltage, and the vertical axis represents the amount of afterimage. In contrast, as illustrated in FIG. 7B, as the amount of change in voltage increases, the amount of noise increases. Here, in FIG. 7B, the horizontal axis represents the absolute value of the amount of change in voltage, and the vertical axis represents the amount of noise.

Accordingly, the larger the amount of change in voltage to reduce the amount of afterimage, the larger the amount of noise, resulting in the reduced S/N ratio of the imaging apparatus. In this case, if the subsequent imaging is performed until the noise has settled down in order to reduce the amount of noise, the period of time until the subsequent imaging is increased, resulting in the reduced usability of the imaging apparatus. In contrast, as the amount of change in voltage decreases, the amount of afterimage is increased, resulting in insufficient prevention of afterimage.

Figure 8:
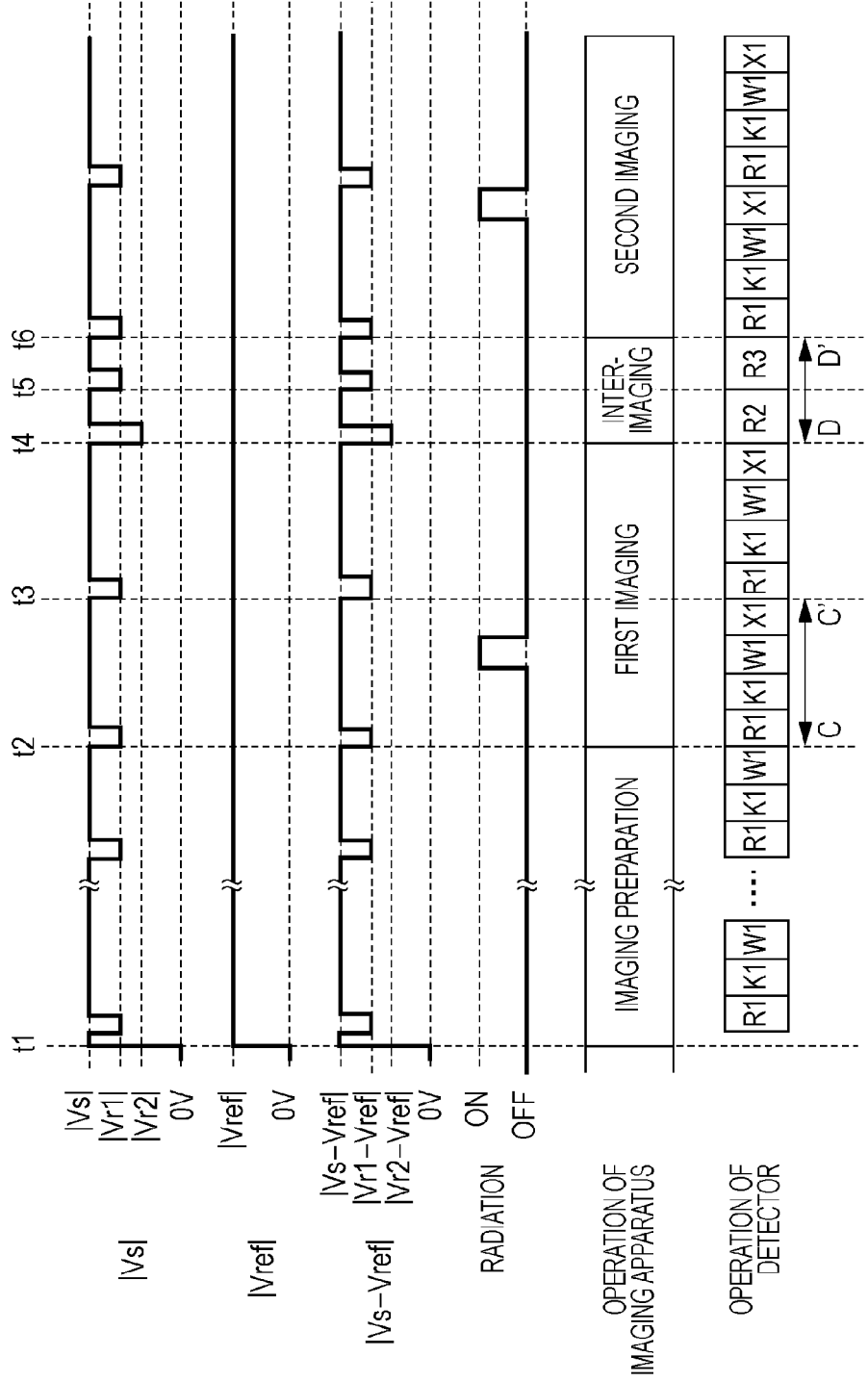
FIG. 8 is a timing chart of the imaging apparatus according to the second embodiment of the present invention.

As a result of intensive study, the present inventor has found the following. A detector is controlled so that, as illustrated in FIG. 8, the detector performs an inter-imaging operation in a plurality of imaging operations including a first imaging operation and a second imaging operation subsequent to the first imaging operation. In the inter-imaging operation, first, the detector is controlled so that the detector performs a first inter-imaging operation between the first imaging operation and the second imaging operation. In the first inter-imaging operation, the detector is controlled so that a second voltage (|Vr2−Vref|) different from a first voltage (|Vs−Vref|) is supplied to the conversion element and the detector performs an initialization operation (refresh operation) for initializing the conversion element. The amount of change in the first voltage (|Vr2−Vs|), which is the absolute value (|Vr2−Vs|) of the difference between the second voltage and the first voltage, is set larger than an amount of change in the second voltage (|Vr1−Vs|) described below. In the first inter-imaging operation, therefore, a large amount of change in voltage is supplied to the conversion element, thereby reducing afterimage as desired. In the first inter-imaging operation, however, noise is increased because a large change in voltage is supplied to the conversion element. Then, the detector is controlled so that the detector performs a second inter-imaging operation between the first inter-imaging operation and the third imaging operation. In the second inter-imaging operation, the detector is controlled so that a third voltage (|Vr1−Vref|) different from the first voltage and the second voltage is supplied to the conversion element and the detector performs an initialization operation. The amount of change in the second voltage (|Vr1−Vs|), which is the absolute value (|Vr1−Vs|) of the difference between the third voltage and the first voltage, is set smaller than the amount of change in the first voltage (|Vr2−Vs|). In the second inter-imaging operation, therefore, a smaller amount of change in voltage than that in the first inter-imaging operation is supplied to the conversion element, thus allowing a reduction in noise, which has been increased in the first inter-imaging operation. In this manner, the present inventor has found that the first inter-imaging operation and the second inter-imaging operation subsequent to the first inter-imaging operation are performed in a plurality of imaging operations, thereby making it possible to prevent an increase in noise while reducing afterimage that has occurred in the preceding imaging operation.

Figure 9B:
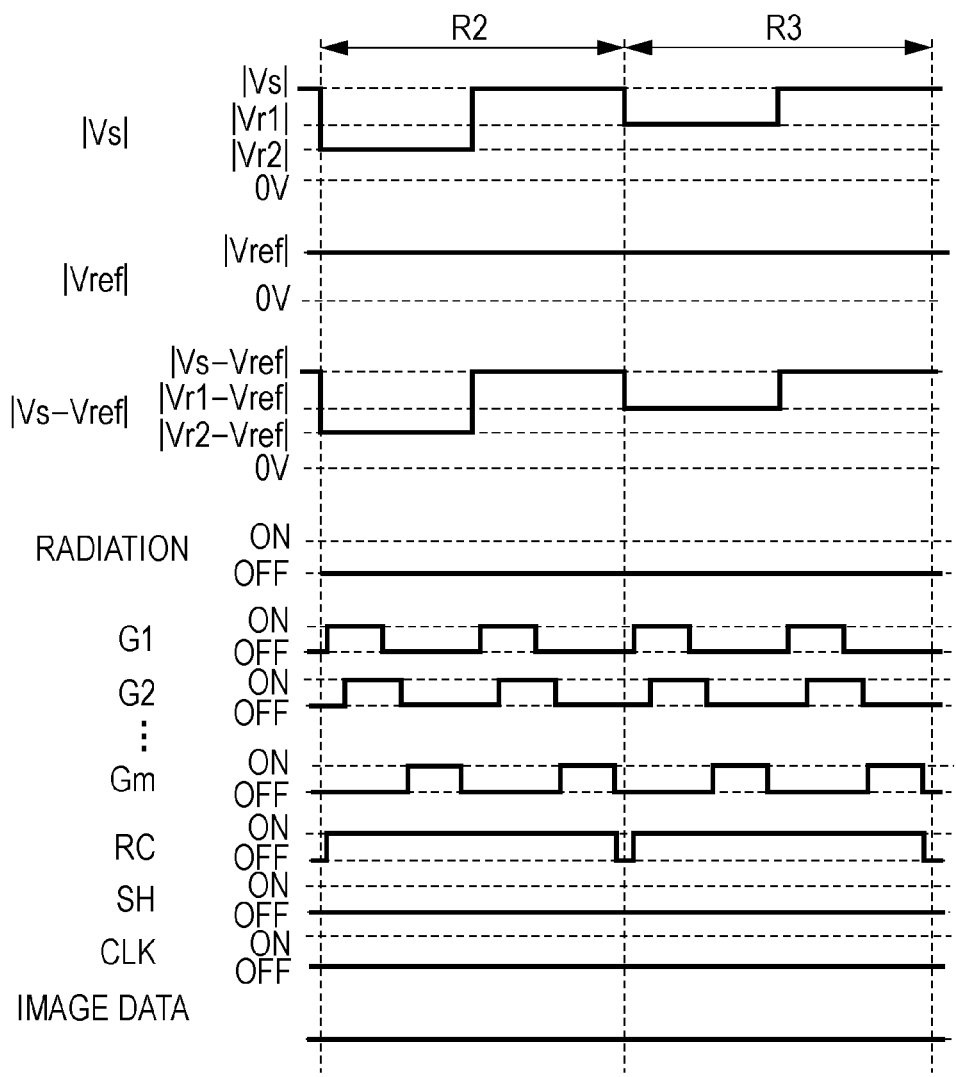
FIG. 9B is a timing chart of the imaging apparatus according to the second embodiment of the present invention.

Next, the operation of the imaging apparatus according to the present invention will be described with reference to FIGS. 8, 9A, and 9B. Here, FIG. 9A illustrates the C-C' section in FIG. 8 in detail, and FIG. 9B illustrates the D-D' section in FIG. 8 in detail. The same components as those illustrated in FIGS. 1, 5A, and 5B according to the first embodiment are assigned the same symbols and numerals, and the detailed description thereof is omitted.

The operation of the imaging apparatus according to the second embodiment is different from the operation of the imaging apparatus according to the first embodiment in the following points. The first point is that the initialization operation K1 is performed by supplying the first voltage |Vs−Vref|, which is the initial voltage prior to the accumulation operation, to the conversion element. The second point is that a first refresh operation R1 is performed as an initialization operation prior to each initialization operation K1. In the first refresh operation R1, first, a second potential Vr1 used for refresh which is different from the first potential Vs is supplied from the first power supply 107a' to the second electrodes 506 of the conversion elements 501. Then, the switching elements 202 are brought into a conductive state sequentially on a row-by-row basis by the drive circuit 102, thereby allowing the conversion elements to be supplied with the second voltage |Vr1−Vref| used for refresh. This can cause the electrons or holes in the electron-hole pairs accumulated between the semiconductor layer 504 and the insulating layer 503 to move towards the second electrode 506 and annihilate. After that, a first bias potential Vs is supplied from the first power supply 107a' to the second electrodes 506 of the conversion elements 501. Then, the switching elements 202 are brought into a conductive state sequentially on a row-by-row basis by the drive circuit 102, thus allowing the initial voltage |Vs−Vref| to be supplied to the conversion elements. Further, the third point is that a second refresh operation R2 is performed as an initialization operation in the first inter-imaging operation, and a third refresh operation R3 is performed as an initialization operation in the second inter-imaging operation. The second refresh operation R2 and the third refresh operation R3 will be described below.

As illustrated in FIG. 9B, in the second refresh operation R2, first, a first bias potential Vs and a second refresh potential Vr2 different from the first refresh potential Vr1 are supplied from the first power supply 107a' to the second electrodes 506 of the conversion elements 501. Then, the switching elements 202 are brought into a conductive state sequentially on a row-by-row basis by the drive circuit 102, thus allowing a second refresh voltage |Vr2−Vref| to be supplied to the conversion elements. The second refresh voltage corresponds to a second voltage according to the present invention. The amount of change in the first voltage (|Vr2−Vs|), which is the difference (|Vr2−Vs|) between the second voltage and the first voltage, is set larger than the amount of change in the second voltage (|Vr1−Vs|) described below. After that, the first potential Vs is supplied from the first power supply 107a' to the second electrodes 506 of the conversion elements 501. Then, the switching elements 202 are brought into a conductive state sequentially on a row-by-row basis by the drive circuit 102, thus allowing the initial voltage |Vs−Vref| to be supplied to the conversion elements. In the second refresh operation R2, therefore, a large amount of change in voltage is supplied to the conversion elements, thereby reducing afterimage as desired. In the second refresh operation R2, however, a large change in voltage is supplied to the conversion elements, resulting in an increase in noise.

Then, in the third refresh operation R3, first, a third potential Vr1 different from the first potential Vs and the second potential Vr2 is supplied from the first power supply 107a' to the second electrodes 506 of the conversion elements 501. Here, the third potential is set to Vr1, which is the same value as the refresh potential in the imaging preparation operation or the imaging operation. Then, the switching elements 202 are brought into a conductive state sequentially on a row-by-row basis by the drive circuit 102, thus allowing a third refresh voltage |Vr1−Vref| to be supplied to the conversion element. The third refresh voltage corresponds to a third voltage according to the present invention. The amount of change in the second voltage (|Vr1−Vs|), which is the difference (|Vr1−Vs|) between the third voltage and the first voltage, is set smaller than the amount of change in the first voltage (|Vr2−Vs|). After that, the first potential Vs is supplied from the first power supply 107a' to the second electrodes 506 of the conversion elements 501. Then, the switching elements 202 are brought into a conductive state sequentially on a row-by-row basis by the drive circuit 102, thus allowing the initial voltage |Vs−Vref| to be supplied to the conversion elements. In the third refresh operation R3, therefore, an amount of change in voltage smaller than that in the second refresh operation R2 is supplied to the conversion element, thus allowing a reduction in noise, which has been increased in the second refresh operation R2.

Here, if the impurity semiconductor layer 505 is made of n-type impurity semiconductor, desirably, the first voltage meets Vs−Vref>0, that is, a voltage of positive polarity. In this case, the second voltage meets Vr2−Vref≤0, that is, a voltage of 0 or less. In this case, the amount of change in the first voltage is one time or more the first voltage. Thus, the polarities of the voltage to be supplied to the MIS conversion elements in the second refresh operation R2 and the voltage to be supplied to the MIS conversion elements in the imaging operation are inverted. This enables all the holes accumulated between the semiconductor layer 504 and the insulating layer 503 to move towards the second electrode 506, and afterimage is significantly reduced. In contrast, the third voltage meets Vr1−Vref>0, that is, a voltage of positive polarity. In this case, the amount of change in the second voltage is less than one time, preferably, less than 0.5 times, the first voltage. Thus, the polarities of the voltage to be supplied to the MIS conversion elements in the third refresh operation R3 and the voltage to be supplied to the MIS conversion elements in the imaging operation are not inverted. This can reduce the amount by which the holes accumulated between the semiconductor layer 504 and the insulating layer 503 move towards the second electrode 506, leading to significant reduction in noise. In this case, the relationship in dimension between the individual potentials meets Vs>Vr1>Vref>Vr2. Alternatively, even if the second voltage meets Vr2−Vref>0, that is, a voltage of positive polarity, the amount of change in the first voltage is preferably 0.8 times or more and less than one times the first voltage. In this case, the amount of change in the second voltage is preferably less than 0.5 times the first voltage, and the relationship in dimension between the individual potentials meets Vs>Vr1>Vr2>Vref. Of course, in a case where the impurity semiconductor layer 505 is made of p-type impurity semiconductor, the signs and relationships in dimension are opposite.

In the foregoing description of this embodiment, the third potential is Vr1, which is the same value as the refresh potential in the imaging preparation operation or the imaging operation. However, the present invention is not limited to this. The third potential may be a potential between the refresh potential in the imaging preparation operation or the imaging operation and the second refresh potential so long as the amount of change in the second voltage meets the above relationship. In a case where the impurity semiconductor layer 505 is made of n-type impurity semiconductor, the third voltage meets Vr3−Vref>0, and the relationship in dimension between the individual potentials meets Vs>Vr1>Vr3>Vr2. Of course, in a case where the impurity semiconductor layer 505 is made of p-type impurity semiconductor, the signs and relationship in dimension are opposite.

Figure 10B:
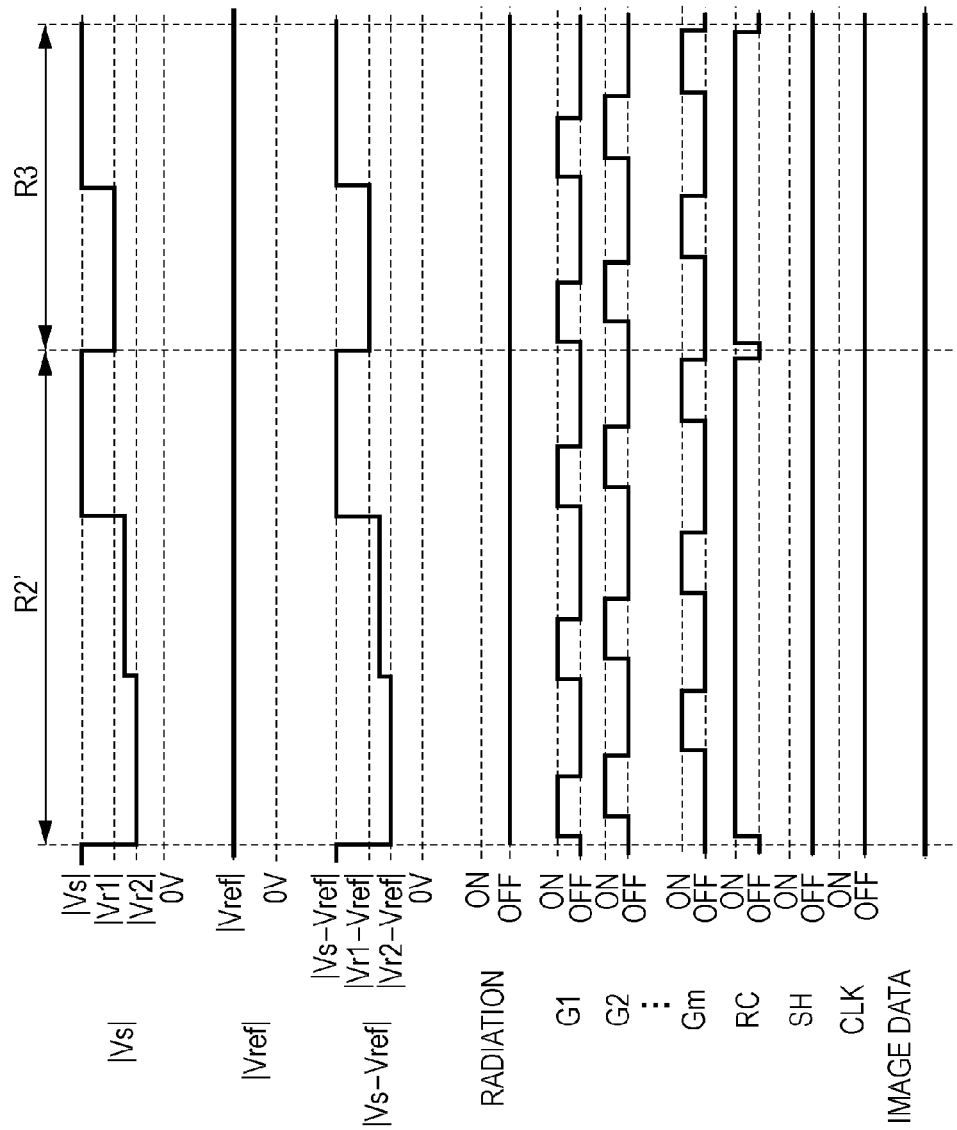
FIG. 10B is a timing chart of another example of the imaging apparatus according to the second embodiment of the present invention.

In the foregoing description of this embodiment, furthermore, the second potential is one potential Vr2. However, the present invention is not limited to this. As illustrated in FIGS. 10A and 10B, in addition to Vr2, a potential (Vr2') between Vr2 and Vr1 may be additionally supplied as the potential to be supplied to the second electrodes 506 of the conversion elements 501 in the first inter-imaging operation to perform a second refresh operation R2'. In this case, in the second refresh operation R2', first, the second voltage Vr2 is supplied from the first power supply 107a' to the second electrodes 506 of the conversion elements 501. Then, the switching elements 202 are brought into a conductive state sequentially on a row-by-row basis by the drive circuit 102, thus allowing a refresh voltage |Vr2−Vref| to be supplied to the conversion elements. Then, the potential Vr2' is supplied from the first power supply 107a' to the second electrodes 506 of the conversion elements 501. Then, the switching elements 202 are brought into a conductive state sequentially on a row-by-row basis by the drive circuit 102, thus allowing the refresh second' voltage |Vr2'−Vref| to be supplied to the conversion elements. The voltages |Vr2−Vref| and |Vr2'−Vref| correspond to a second voltage according to the present invention. After that, the first bias potential Vs is supplied from the first power supply 107a' to the second electrodes 506 of the conversion elements 501. Then, the switching elements 202 are brought into a conductive state sequentially on a row-by-row basis by the drive circuit 102, thus allowing the initial voltage

|Vs−Vref| to be supplied to the conversion elements. In addition, in each inter-imaging operation, only an initialization operation may be performed without accumulation operations being performed. In this case, the voltage to be supplied to the conversion element may be gradually changed.

The embodiments of the present invention can also be implemented by, for example, the computer included in the control unit 106 or the control computer 108 executing a program. Means for supplying the program to the computer, for example, a computer-readable recording medium having the program recorded thereon, such as a CD-ROM, or a transmission medium that transmits the program, such as the Internet, can also be applied as an embodiment of the present invention. In addition, the program described above can also be applied as an embodiment of the present invention. The above-described program, recording medium, transmission medium, and program product are embraced by the present invention. In addition, an invention based on combinations readily discernable from the first or second embodiment is also embraced by the present invention.

The present invention is not intended to be limited to the foregoing embodiments, and a variety of changes and modifications can be made without departing from the spirit and scope of the present invention. Therefore, the claims which follow are appended in order to clearly define the scope of the present invention.

According to the present invention, an imaging apparatus capable of acquiring an image with a high S/N ratio while preventing an afterimage even with short imaging operation intervals can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of International Patent Application No. PCT/JP2011/072322, filed Sep. 29, 2011, which is hereby incorporated by reference herein in its entirety.

The invention claimed is:

1. An imaging apparatus comprising:
a detector including a plurality of conversion elements each having a first electrode, a second electrode, and a semiconductor layer disposed between the first electrode and the second electrode and converting radiation or light into charge, the detector performing an imaging operation of outputting an electrical signal based on the charge;
a power supply unit that supplies a first voltage to the conversion elements for enabling the conversion elements to convert the radiation or light into the electric charge in the imaging operation to the conversion elements; and
a control unit that controls the detector and the power supply unit,
wherein the control unit controls the detector and the power supply unit to perform a first inter-imaging operation in which a second voltage different from the first voltage is supplied to the conversion elements, during a period between, in the imaging operation which is performed a plurality of times, a first imaging operation and a second imaging operation subsequent to the first imaging operation, and a second inter-imaging operation in which a third voltage different from the first voltage and the second voltage is supplied, during the period, subsequently to the first inter-imaging operation, and wherein the absolute value of the difference between the third voltage and the first voltage is smaller than the absolute value of the difference between the second voltage and the first voltage.

2. The imaging apparatus according to claim 1, wherein each of the conversion elements includes a photodiode, and
wherein the first voltage is a reverse voltage.

3. The imaging apparatus according to claim 2, wherein the second voltage is a reverse voltage larger than the first voltage, and
wherein the third voltage is a reverse voltage smaller than the first voltage or a reverse voltage larger than the first voltage and smaller than the second voltage.

4. The imaging apparatus according to claim 2, wherein the second voltage is a reverse voltage smaller than the first voltage, and
wherein the third voltage is a reverse voltage smaller than the first voltage or a reverse voltage larger than the first voltage.

5. The imaging apparatus according to claim 2, wherein the second voltage is a forward voltage, and
wherein the third voltage is a reverse voltage smaller than the first voltage or a reverse voltage larger than the first voltage.

6. The imaging apparatus according to claim 2, wherein the detector includes a detection unit having a plurality of pixels arranged in a matrix, each pixel including the conversion element and a switching element connected to the first electrode, a drive circuit that brings the switching element into a conductive state to output the electrical signal from the detection unit, a signal line that transmits the electrical signal, and a read circuit that reads the electrical signal via the signal line,
wherein the power supply unit includes a first power supply connected to the second electrode, and a second power supply connected to the signal line via the read circuit,
wherein the second power supply supplies a reference potential to the signal line, and
wherein the first power supply supplies a first potential to the second electrode in the imaging operation, supplies a second potential different from the first potential to the second electrode in the first inter-imaging operation, and supplies a third potential different from the first potential and the second potential in the second inter-imaging operation.

7. The imaging apparatus according to claim 1 wherein the conversion element is an MIS conversion element having the first electrode, the second electrode, the semiconductor layer, an insulating layer disposed between the first electrode and the semiconductor layer, and an impurity semiconductor layer disposed between the semiconductor layer and the second electrode, and
wherein the power supply unit supplies the second voltage or the third voltage between the first electrode and the second electrode in order to allow the detector to perform a refresh operation of causing electrons or holes in electron-hole pairs accumulated between the semiconductor layer and the insulating layer within charge generated in the semiconductor layer due to the first voltage being supplied to the conversion element to move towards the second electrode and annihilate.

8. The imaging apparatus according to claim 7, wherein the detector includes a detection unit having a plurality of pixels arranged in a matrix, each pixel including the conversion element and a switching element connected to the first electrode, a drive circuit that brings the switching element into a conductive state to output the electrical signal from the detection unit, a signal line that transmits the electrical signal, and a read circuit that reads the electrical signal via the signal line,
  wherein the power supply unit includes a first power supply connected to the second electrode, and a second power supply connected to the signal line via the read circuit,
  wherein the second power supply supplies a reference potential to the signal line, and
  wherein the first power supply supplies a first potential to the second electrode in the imaging operation, supplies a second potential different from the first potential to the second electrode in the first inter-imaging operation, and supplies a third potential different from the first potential and the second potential in the second inter-imaging operation.

9. The imaging apparatus according to claim 8, wherein the impurity semiconductor layer is an n-type impurity semiconductor layer, and
  wherein if the first potential is denoted by Vs, the second potential is denoted by Vr2, the third potential is denoted by Vr1, and the potential to be supplied from the second power supply to the signal line is denoted by Vref, the following relationships are satisfied:

$Vs-Vref>0$ $Vr1-Vref>0$ $Vr2-Vref\leq 0$ $Vs>Vr1>Vref>Vr2.$

10. The imaging apparatus according to claim 8, wherein the impurity semiconductor layer is an n-type impurity semiconductor layer, and
  if the first potential is denoted by Vs, the second potential is denoted by Vr2, the third potential is denoted by Vr1, and the potential to be supplied from the second power supply to the signal line is denoted by Vref, the following relationships are satisfied:

$Vs-Vref>0$ $Vr1-Vref>0$ $Vr2-Vref>0$ $Vs>Vr1>Vr2>Vref$ $0.8\times|Vs-Vref|\leq|Vr2-Vs|<|Vs-Vref|$ $|Vr1-Vs|<0.5\times|Vs-Vref|.$ 11. An imaging system comprising:
  the imaging apparatus according to claim 1; and
  a control computer that sends a control signal to the control unit.

12. A method for controlling an imaging apparatus which includes a detector including a plurality of conversion elements each having a first electrode, a second electrode, and a semiconductor layer disposed between the first electrode and the second electrode and converting radiation or light into an electric charge, the method comprising:
  performing a first imaging operation for allowing the detector to output an electrical signal based on the charge converted from the radiation or light by the conversion element to which a first voltage for allowing the conversion element to convert radiation or light into charge has been supplied;
  performing subsequently to the first imaging operation a first inter-imaging operation in which a second voltage different from the first voltage is supplied to the conversion element;
  performing subsequently to the first inter-imaging operation a second inter-imaging operation in which a third voltage different from the first voltage and the second voltage is supplied to the conversion element; and
  performing subsequently to the second inter-imaging operation a second imaging operation for allowing the detector to output an electrical signal based on the charge converted from radiation or light by the conversion element to which the first voltage has been supplied,
  wherein the absolute value of the difference between the third voltage and the first voltage is smaller than the absolute value of the difference between the second voltage and the first voltage.

13. A method for controlling an imaging apparatus which includes a detector including a plurality of conversion elements for converting radiation or light into an electric charge and a power supply unit for supplying voltage to the conversion elements, the method comprising:
  supplying a first voltage to the conversion elements for enabling the conversion elements to convert the radiation or light into the electric charge in a first imaging operation of outputting an electrical signal based on the electric charge; and
  controlling the detector and the power supply unit to perform a first inter-imaging operation in which a second voltage different from the first voltage is supplied to the conversion elements, during a period between the first imaging operation and a second imaging operation subsequent to the first imaging operation, and a second inter-imaging operation in which a third voltage different from the first voltage and the second voltage is supplied, during the period, subsequently to the first inter-imaging operation,
  wherein the absolute value of the difference between the third voltage and the first voltage is smaller than the absolute value of the difference between the second voltage and the first voltage.

* * * * *